(12) United States Patent
Anderson et al.

(10) Patent No.: US 7,096,148 B2
(45) Date of Patent: Aug. 22, 2006

(54) MAGNETIC TRACKING SYSTEM

(75) Inventors: Peter T. Anderson, Andover, MA (US); Gerald L. Beauregard, Hampton, NH (US); Christopher D. Cherry, Bolton, MA (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 22 days.

(21) Appl. No.: 11/024,925

(22) Filed: Dec. 22, 2004

(65) Prior Publication Data

US 2005/0165297 A1 Jul. 28, 2005

Related U.S. Application Data

(62) Division of application No. 10/713,514, filed on Nov. 14, 2003, now Pat. No. 6,980,921, which is a division of application No. 10/108,197, filed on Mar. 27, 2002, now Pat. No. 6,774,624.

(51) Int. Cl.
*G06G 15/00* (2006.01)
*G01B 7/14* (2006.01)

(52) U.S. Cl. ............... 702/134; 324/207.17; 600/424; 702/150

(58) Field of Classification Search ........... 702/134, 702/150–153; 324/207.11, 207.12, 207.17, 324/207.18, 318; 342/448; 343/895; 600/424, 600/429
See application file for complete search history.

(56) References Cited

U.S. PATENT DOCUMENTS

| | | | |
|---|---|---|---|
| 3,983,474 A | 9/1976 | Kuipers | 324/207.18 |
| 4,054,881 A | 10/1977 | Raab | 342/448 |
| 4,109,199 A | 8/1978 | Ball et al. | 324/202 |
| 4,316,866 A | 2/1982 | Martin | 264/157 |
| 4,642,786 A | 2/1987 | Hansen | 702/153 |
| 4,737,794 A | 4/1988 | Jones | 342/448 |
| 4,742,356 A | 5/1988 | Kuipers | 342/448 |
| 4,849,692 A | 7/1989 | Blood | 324/207.26 |
| 4,945,305 A | 7/1990 | Blood | 324/207.17 |
| 5,172,056 A | 12/1992 | Voisin | 324/207.17 |
| 5,307,072 A | 4/1994 | Jones, Jr. | 342/147 |
| 5,453,686 A | 9/1995 | Anderson | 324/207.17 |
| 5,558,091 A | 9/1996 | Acker et al. | 600/424 |

(Continued)

FOREIGN PATENT DOCUMENTS

WO WO 00/36428 A1 6/2000

(Continued)

OTHER PUBLICATIONS

"A Source of Accurately Calculable Quasi-Static Magnetic Field," by Peter Traneus Anderson (Oct. 2001).

(Continued)

*Primary Examiner*—Michael Nghiem
*Assistant Examiner*—John Le
(74) *Attorney, Agent, or Firm*—McAndrews, Held & Malloy, Ltd.; Peter D. Vogel; Michael A. Dellapenna

(57) ABSTRACT

The present invention provides an electromagnetic tracking system that includes a field generator and a field sensor arranged to generate and detect, respectively, an electromagnetic field. Both the transmitter and receiver coils are connected to signal conditioning and processing circuitry to provide outputs indicative of the coil signals. A processor operates on the signals to determine the coordinates of the sensing assembly relative to the generator assembly. The signal processor produces ratiometric outputs, and applies a mutual inductance model to solve for position/orientation coordinates. In some embodiments, a disturber in the form of a conductive ring or a sheath is disposed about an interfering piece of equipment to moderate and standardize disturbances due to eddy currents.

7 Claims, 10 Drawing Sheets

U.S. PATENT DOCUMENTS

| | | | |
|---|---|---|---|
| 5,600,330 A | 2/1997 | Blood | 342/463 |
| 5,640,170 A | 6/1997 | Anderson | 343/895 |
| 5,646,524 A | 7/1997 | Gilboa | 324/207.17 |
| 5,767,669 A | 6/1998 | Hansen et al. | 324/207.12 |
| 5,967,980 A | 10/1999 | Ferre et al. | 600/424 |
| 6,073,043 A | 6/2000 | Schneider | 600/424 |
| 6,095,150 A | 8/2000 | Panescu et al. | 128/899 |
| 6,172,499 B1 | 1/2001 | Ashe | 324/207.12 |
| 6,177,792 B1 | 1/2001 | Govari et al. | 324/207.12 |
| 6,188,355 B1 | 2/2001 | Gilboa | 342/448 |
| 6,223,066 B1 | 4/2001 | Govari | 600/424 |
| 6,226,547 B1 | 5/2001 | Lockhart et al. | 600/424 |
| 6,233,476 B1 | 5/2001 | Stommer et al. | 600/424 |
| 6,246,231 B1 | 6/2001 | Ashe | 324/207.17 |
| 6,369,564 B1 * | 4/2002 | Khalfin et al. | 324/207.17 |
| 6,380,732 B1 | 4/2002 | Gilboa | 324/207.17 |
| 6,427,079 B1 | 7/2002 | Schneider et al. | 600/424 |
| 6,534,982 B1 | 3/2003 | Jakab | 324/318 |
| 6,615,155 B1 | 9/2003 | Gilboa | 702/150 |
| 6,636,757 B1 | 10/2003 | Jascob et al. | 600/424 |
| 2001/0045826 A1 | 11/2001 | Schneider | 324/207.17 |
| 2001/0047133 A1 | 11/2001 | Gilboa et al. | 600/429 |

FOREIGN PATENT DOCUMENTS

WO     WO 01/69594 A1     9/2001

OTHER PUBLICATIONS

Jackson, John D. "Classical Electrodynamics" (1975).
Brogan, William L. "Modern Control Theory" (1991).
Horn, Berthold "Closed-form solution of absolute orientation using unit quaternions" J.Op Soc. Am., vol. 4 Apr. 1997.
Raab, Frederick H. "Quasi static magnetic field technique for determining position and orientation." IEEE Transactions on Geoscience and Remote Sensing, vol. GE-19, Oct. 1981 (pp. 235-243).
Smythe, William R. "Static and Dynamic Electricity" (1989) (pp. 333 and 415).
Zachmann, Gabriel "Distortion correction of magnetic fields for position tracking" Computer Graphics Int'l (CGI 1997).
Anderson, "An electromagnetic tracking system using printed circuit coils," from IEEE Antennas and Propagation Society International Symposium, 2001, vol. 1, pp. 304-307, Jul. 2001.
Plotkin and Paperno, "3D magnetic tracking of a single subminiature coil with a large 2D array of Uniaxial transmitters," IEEE Transactions on Magnetics, Col. 39 No. 5, Sep. 2003, pp. 3295-3297.

* cited by examiner

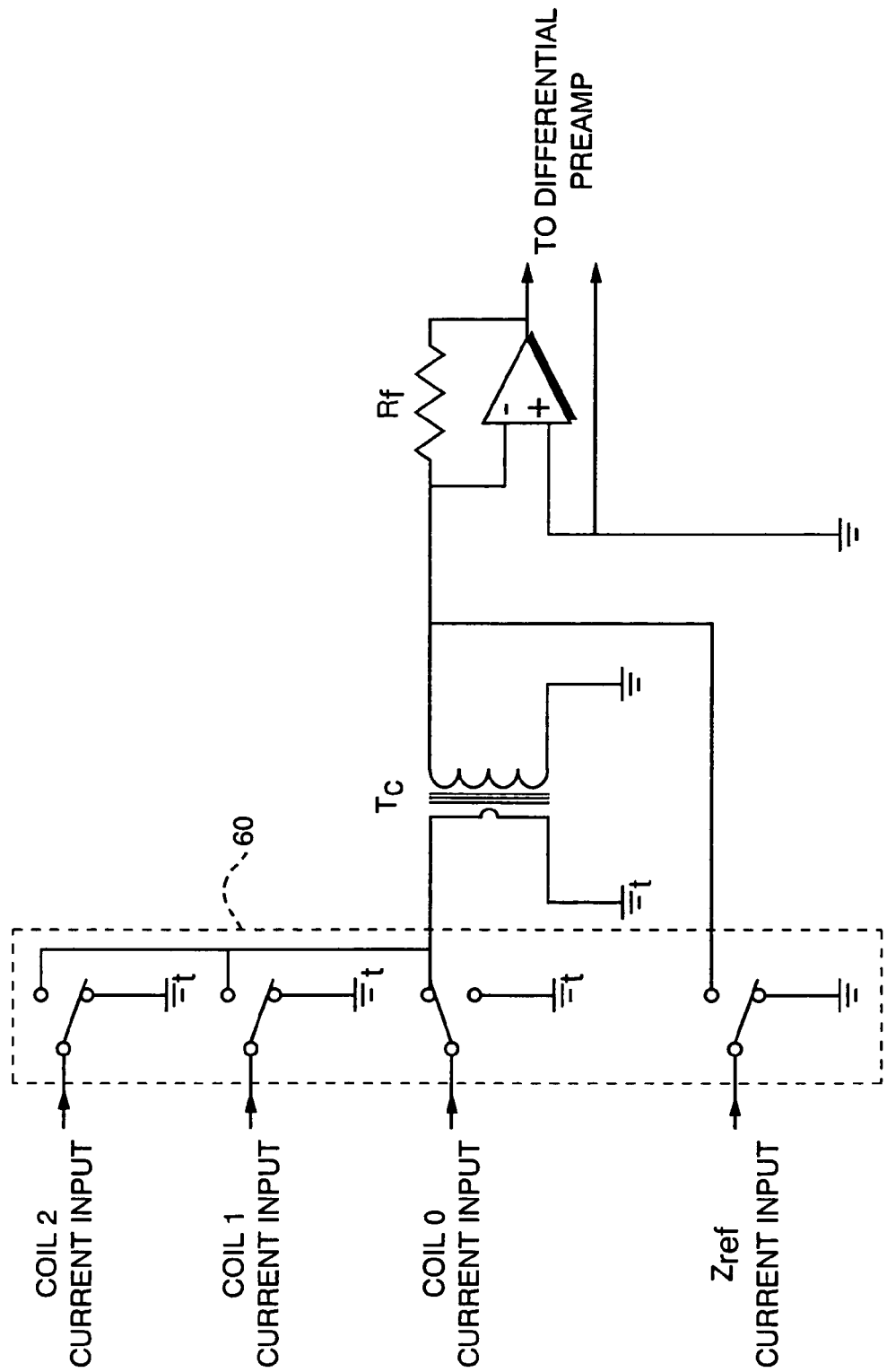

MAGNETIC TRACKING SYSTEM

RELATED APPLICATIONS

This application is a divisional of U.S. patent application Ser. No. 10/713,514, entitled "Magnetic Tracking System," filed Nov. 14, 2003, now U.S. Pat. No. 6,980,921, which is a divisional of U.S. patent application Ser. No. 10/108,197, entitled "Magnetic Tracking System," filed Mar. 27, 2002, now U.S. Pat. No. 6,774,624. U.S. patent application Ser. No. 10/713,514 and U.S. Pat. No. 6,774,624 are both hereby expressly incorporated by reference in their entireties.

BACKGROUND OF THE INVENTION

The present invention relates to magnetic tracking systems of the type wherein a magnetic field is established in a relevant work area, and one Or more magnetic field sensors are operated to sense values of a local magnetic field and are processed to determine the position of a tool, instrument or other identified object. In general, such systems operate using a field generating element or assembly, and a field sensing element or assembly, often in conjunction with other position determining elements, such as robotic stepper or optical tracker assemblies to track the relative changes in position between one or more fixed points or structures in the physical environment or associated images, and one or more moving or non-visible points or structures in the work arena.

Magnetic field generating or sensing assemblies for tracking may be implemented in various ways, with conventional analog wire coils forming current loops or paths, or with semiconductor or microlithographically-formed conductive leads or circuit board traces forming current paths, arranged in an appropriate geometry to generate or sense the desired field components. There may be a symmetry or duality between the generating or sensing elements. Thus, for example in many cases it is possible to have a small multi-coil array that generates a spatially distributed magnetic field and a similar or even identical array that senses the field so generated. Small coils offer the prospect of generating, to a close approximation, dipole fields, although small size may limit the attainable field strength or the achievable level of detection signal amplitude. The generating and sensing constructions may alternatively employ different scales, for example, with relatively large and/or high current coils to establish magnetic field components along different axes, and smaller, or more localized coil assemblies for sensing field values. Smaller coils, whether for sensing or generating, may, for example, be fastened to the body, or attached to workplace or surgical instruments, or to catheters or other body-inserted devices, to sense the magnetic field and track position of the attached structure.

In general, it is the aim of such magnetic tracking assemblies to define the spatial coordinates (e.g., position and orientation coordinates, either absolute or relative) where the movable magnetic assembly is located at a given instant in time. It is therefore necessary to characterize the magnetic field distribution or signal values with some degree of accuracy, and also necessary to accurately detect the field. The field distribution may be determined by a combination of field modeling and empirical field mapping. The latter, for example, may be carried out as a calibration or an initialization step, and may be performed to correct a theoretical field distribution for the presence of interfering structures. In any case, the spatial coordinates are generally computed for one magnetic assembly (transmitter or sensor) with respect to the other magnetic assembly (sensor or transmitter). Typically, one of these assemblies is itself fixed.

One area in which magnetic tracking has been useful is the area of image guided surgery. Typical image guided surgical systems acquire a set of images of an operative region of a patient's body, and track a surgical tool or instrument in relation to one or more sets of coordinates, e.g., spatial coordinates of the surgical work arena, the coordinates of the images themselves, or a target feature of the patient's anatomy. At the present time, such systems have been developed or proposed for a number of surgical procedures such as brain surgery and arthroscopic procedures on the knee, wrist, shoulder or spine, as well as certain types of angiography, cardiac or other interventional radiological procedures and biopsies. Such procedures may also involve preoperative or intraoperative x-ray images being taken to correct the position of and refine the display of, or otherwise navigate a tool or instrument involved in the procedure in relation to anatomical features of interest.

Several areas of surgery have required very precise planning and control. Such tracking is useful for the placement of an elongated probe, radiation needle, fastener or other article in tissue or bone that is internal or is otherwise positioned so that it is difficult to view directly. For brain surgery, stereotactic frames may be used to define the entry point, probe angle and probe depth to access a site in the brain. Furthermore, many of the foregoing techniques may be used in conjunction with previously-compiled three-dimensional diagnostic images such as MRI, PET or CT scan images to provide accurate tissue coordinates to which the tracked physical elements may be referenced. Such systems offer valuable improvements for procedures such as placement of pedicle screws in the spine, where visual and fluoroscopic imaging directions cannot capture the axial view that would be required to safely orient the insertion path through bony material close to the spinal cord.

When used with existing CT, PET or MRI image sets, the previously recorded diagnostic image sets, by virtue of their controlled scan formation and the spatial mathematics of their reconstruction algorithms, define a high precision three dimensional rectilinear coordinate system. However, even when provided with such reference images it is necessary to correlate and fit available measurement and views and anatomical features visible from the surface, with features in the diagnostic images and with the external coordinates of the tools being employed. This is often done by providing implanted fiducials, by adding external visible or trackable markers that may be imaged, and by enabling a surgeon or radiologist to use a keyboard or mouse to identify fiducials or features in the various images, and thus map common sets of coordinate registration points in the different images. Given a fit of spatial points to image points, software may then track changing positions in an automated way (for example, simply transforming the coordinates that are output by an external coordinate measurement device, such as a suitably programmed off-the-shelf optical tracking assembly.) Instead of correlating image positions of a set of imageable fiducials appearing in fluoroscopic or CT images, such systems can also operate with simple optical tracking, employing an initialization protocol wherein the surgeon touches or points at a number of bony prominences or other recognizable anatomic features in order to define the external coordinates in relation to the patient anatomy and to initiate software tracking of those features.

For such applications, electromagnetic tracking offers the advantage that its position-defining field, a magnetic field, penetrates the body without attenuation or change so that tracking may continue during a surgical procedure, unimpaired by the blocking that occurs with visible light trackers (e.g., due to operating room personnel moving into positions that obstruct the line-of-sight paths required by optical trackers). Optical or ultrasonic tracking, by contrast, may require a larger or excess number of line-of-sight paths, and corresponding transponders and/or detectors to assure that triangulation is always possible despite occluded pathways. The body-penetrating electromagnetic fields also allow one to track locations or movements inside the body with minimal resort to the fluoroscopic or ultrasound techniques normally required for visualization.

Among electromagnetic tracking techniques, several principal approaches are known. In one, relatively large Helmholtz coils establish well defined and highly uniform independent magnetic field components or gradients along each of the X, Y and Z axes in a work arena, and the static field components are detected by a localized detector to determine position coordinates. This approach has been proposed, for example, for cranial surgery, where such coils may define a suitably localized region encompassing the entire operative arena. Another principal approach involves using time-varying dipole fields e.g., dipole fields established by driving field-generating coils with an AC current signal. While the latter approach offers some processing advantages (such as being able to synchronously demodulate induced signals, and thus cumulate detected signal values to enhance sensitivity, and also the ability to establish the X, Y and Z field components at different frequencies so that detected sensor output signals may be separated or even demodulated simultaneously), it has the disadvantage that varying magnetic fields induce eddy currents in conductive structures found within the field. Induced currents themselves then generate secondary magnetic fields, thus introducing distortions into the expected or calibrated field distribution. Conductive or metal structures are in fact commonly present in a tracking environment, whether it be an avionics, surgical or industrial tracking environment.

The latter problem has historically been addressed by the observation that for a fixed metal disturber located at least twice as far from the field generator as is the field sensor, the induced disturbance will be low, e.g., under one percent, so that by restricting the tracked arena to a region sufficiently removed from the disturbing structure, accuracy may be achieved. However, this approach may be unrealistically restrictive for certain applications, including some image guided surgery applications, where highly disturbing equipment (such as the imaging assembly of a fluoroscope) is necessarily placed as close as possible to the work arena in which tracking is to occur. Another common alternative approach would be to map the disturbed fields or detected signal levels that occur close to the distorters present in the work arena, so that a processor can more accurately determine coordinates from the run time field values or the induced signals detected by a sensor. However, as a practical matter, such mapping is not only likely to require a time-consuming preliminary set-up operation, but may require that the set-up be carried out afresh for each new arrangement of operating room equipment that introduces different distortions, i.e., when equipment is changed or moved.

In addition to the practical problem of accurately detecting the field, there is the theoretical problem of converting the signal measurements into position and orientation coordinates.

On a fundamental level, the task that must be addressed by any electromagnetic tracking system is to computationally determine a unique position from the various measured parameters (typically induced voltages indicative of field strength). Often the relevant equations have several solutions, and care must be taken to operate within a single-valued domain (typically a hemisphere, quadrant or octant), thus limiting the selection of the initial generator or receiver fixed locations to establish a sufficiently well behaved field region, and restricting the allowable work arena in relation thereto, or else providing additional, or extrinsic data inputs to resolve ambiguities or refine computations. Beyond encountering multi-valued coordinate solutions, the accuracy of the coordinate determination processing may depend quite critically on the relative positions of generating and sensing elements. Processing equations may break down or solutions may become poorly defined as the sensing or generating element approaches or crosses a particular plane or axis, or one of its pitch, yaw or roll angle coordinates approaches 0 or 90 degrees, becomes too acute, or becomes too oblique.

Another practical problem stems from the dynamic range of the sensed signals, which varies greatly with distance/position, and may drop to quite low levels with increasing distance from the transmitter, or with decreasing size of the generating or sensing coils. Often, as a field unit moves to different positions, different gains must be determined on the fly, or additional gain stages must be used in order to obtain adequate signal values. This introduces some complexity and potential for error in normalizing the signals to accurately fit together readings from two different or even closely contiguous regions.

Thus, while magnetic tracking offers certain significant advantages, particularly for surgical applications, there remains a need for improved systems and processing to enhance accuracy of coordinate determinations.

Accordingly, it would be desirable to provide an electromagnetic tracker of enhanced accuracy.

It would also be desirable to provide an electromagnetic tracker having enhanced immunity to common field distortions.

SUMMARY OF THE INVENTION

One or more of these and other desirable features are obtained in an electromagnetic tracking system wherein a field generating unit and a field sensing unit are arranged to generate and to sense, respectively an electromagnetic field in an arena of interest. At least one of the units is movable, and the units are connected to signal conditioning and processing circuitry that detects the levels of the transmitter drive signals and the received signals, ratiometrically combining them to form a matrix representative of the mutual inductance of each of the pairs of component coils. The mutual inductance information, providing functions of the relative positions and orientations of the two units, is then processed to determine corresponding coordinates.

Since mutual inductance is a symmetric property, i.e., depending simply on the geometries of the transmission and receiving coils and their relative positions, the system may interchange transmitter and receiver units, employing quite small coil assemblies, yet use a model that gives a direct computation of coordinates without excessive iterative approximations, and without resort to the multitude of gain level and other normalization corrections otherwise typically needed when working from magnetic field intensity measurements. The equations may be processed and solved in real time to effect surgical or other position tracking, and various corrections and calibration of signal magnitude (e.g., for cross-coupling of coils or for finite-size and non-circular coil geometries) are readily implemented.

In accordance with another aspect of the invention, the magnetic tracking systems of the invention may employ signal conditioning or processing electronics in which relevant signals pass through fixed gain amplifiers to high precision (e.g, 24 bit A/D) digital converters. This bit size encompasses a dynamic range effective for multi-bit representation of signals encountered at all regions of the intended tracking area, thereby avoiding the need for variable gain or AGC elements, or for multiple or different preamps having different gain levels, as one coil assembly moves further from the other. Thus, the provision of a common preamplifier with a high precision sampler eliminates patching and the errors due to inaccurate gain ratios between gain states.

In accordance with another or further aspect of the invention, the processor employs a model or set of equations that operate, with the sensor output values, to determine the position/orientation coordinates of the transmitter/receiver assemblies, and when a tracked magnetic coil assembly element approaches a singular region, i.e., a plane or region where the model becomes ill-defined, inaccurate or lacks a solution in the coordinate system, the processor operates by transforming to a coordinate representation in which the detected values lie in a well-defined or non-singular region. The processor then solves to determine a coordinate measurement, and transforms back to the underlying or original coordinate system.

In accordance with another aspect, an operating room system of the invention may employ a conductive shield, or a sheath structure configured to fit about or contain an interfering component or piece of equipment The sheath standardizes the magnetic field disturbance introduced by the component In some instances the sheath may be a metal cylinder, dimensioned to enclose the disturbing piece of equipment. The sheath or cylinder may be formed of sheet metal of a gauge such that eddy currents are induced by the magnetic field, thus giving rise to a standardized field disturbance originating at a contour or surface external to the equipment. Alternatively, other suitable conductive materials, such as a carbon fiber composite material, may be used. The sheath also moderates or effectively nulls electromagnetic disturbances originating within its contour, e.g., at the underlying piece of equipment disposed within the sheath. The inclusion of this standardized disturbance in a system of the invention permits the interchange of different pieces of equipment without introducing excessive variations in resulting local disturbance characteristics. Disturbances may thus be mapped, or even modeled, in a single initial set up operation, without necessitating compilation of a new disturbance map for each new piece of equipment.

In accordance with another or additional aspect of the invention, rather than simply introducing a sheath to form a standardized disturbance, the processor may model such a disturbance. For example, the processor may model a conductive sheath fitted about a certain region as a conductive ring or cylinder at that region (using the known dimensions and behavior characteristics of the sheet metal material). The modeled disturbance may then be added to the stored values of a map of the undisturbed electromagnetic field to form an enhanced field map, or may be otherwise applied to enhance accuracy of tracking determinations. The modeled field may also be used to provide a seed value for determining position and orientation coordinates. A fitting procedure then refines the initial value to enhance the accuracy of the P&O determination.

BRIEF DESCRIPTION OF THE DRAWINGS

These and other features of the invention will be understood from the description below and accompanying claims, taken together with the Figures illustrating embodiments thereof wherein:

FIGS. 5A–5F illustrate circuit details of some exemplary embodiments;

DETAILED DESCRIPTION

Figure 1:
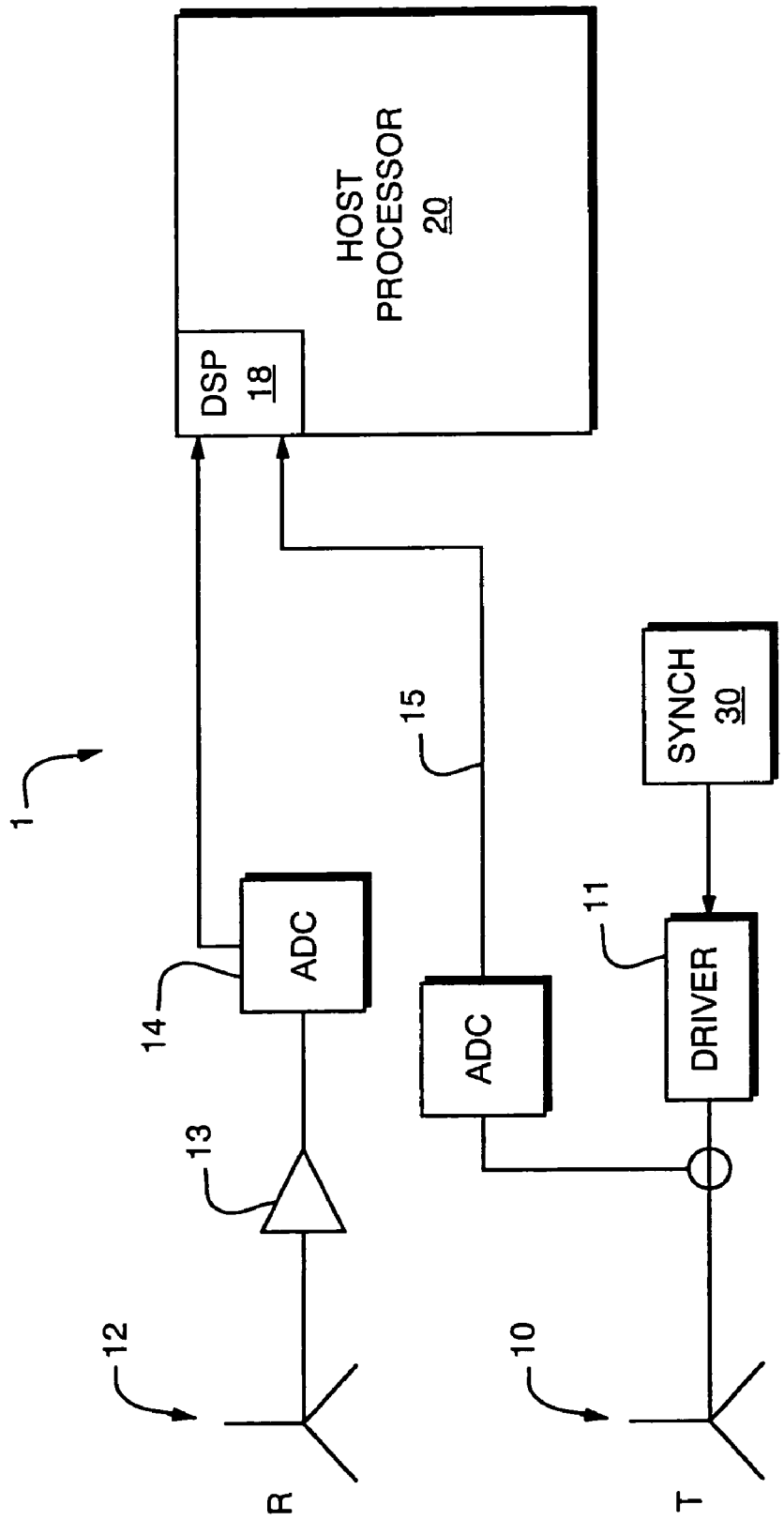
FIG. 1 illustrates basic hardware elements of a tracking system in accordance with the present invention.

The present invention is an improved electromagnetic tracking system which may, by way of example, be employed in an operating room or clinical setting to determine the position and orientation of an object such as a catheter, surgical tool, marker or the like in relation to other physical structures, or in relation to images that may, for example, have coordinates assigned thereto by other means, such as via coordinatized 3-D image sets, position-defining frames, or correlation with imaged or tracked fiducials or markers. A great number of such systems are known, being described for example in U.S. Pat. No. 5,967,980 and related patents of M. Ferre et al, No. 5,307,072, and others, so the features of such systems will not be further described here.

As relevant to a first aspect of the present invention, an electromagnetic tracking system includes a magnetic field generator and a magnetic field sensor together with signal conditioning circuitry and a processor for processing the conditioned signals. The generator and sensor are also referred to as transmitter and receiver below. In general, a varying current injected into one coil assembly produces a magnetic field, and this field induces a voltage in the other coil assembly. The induced voltage V is proportional to the rate of change of the applied current I, with a constant of proportionality equal to $L_m$, the mutual inductance. According to one aspect of the invention, a magnetic tracking system is configured to apply the transmitter drive signals and the induced receiver assembly signals to determine mutual inductances, from which the processor then determines the coordinates—i.e., the position and orientation coordinates, or simply "P&O"—of one coil assembly of the system with respect to the other coil assembly.

For two closed circuits the mutual inductance is given by Neumann's formula, and is equal to an expression which depends only on the geometry of the closed circuits (e.g., the coils), and not on the electronics used to measure the mutual inductance. Since the mutual inductance $L_m$ is a ratio independent of applied current, wave form or frequency, it remains a well defined measurement parameter under a wide variety of conditions, offering improved performance in real operating environments. With three transmitting coils and three receiving coils, nine mutual inductances provide an over-determined system for derivation of the position and orientation coordinates.

In some embodiments, the roles of transmitter and receiver assemblies may be interchanged, each comprising a substantially identical three axis dipole coil assembly. Preferably these assemblies are built so the three coils of an assembly each exhibit the same effective area, are oriented orthogonally to one another, and are centered at the same point. For many of the applications alluded to above, the coils are quite small and ideally are small enough (compared to the transmitter-receiver distance) that they may, as an initial approximation, be considered to exhibit dipole behavior. However, more generally, the system includes embodiments discussed more fully below, wherein one or more of the coils are modeled or their signals processed as finite size transmitter or receiver.

It should be noted that the closed magnetic generating or receiving circuit includes the coil, its connecting cable and some electronics to which the cable is connected. In accordance with a preferred embodiment of the present invention discussed further below, contributions of these extrinsic or ancillary circuit elements are reduced or eliminated, permitting a simple and highly accurate model of the coil alone with a direct short across the coil leads.

FIG. 1 schematically illustrates a basic measurement system 1 employed in a prototype embodiment A transmitter assembly 10 is driven by a transmitter driver 111 to produce a magnetic field, while a receiver assembly 12 responds to the magnetic field by producing induced signals, coupling the signals induced therein to a receiver voltage preamp 13 and an analog to digital converter 14. The transmitter assembly 10 and receiver assembly 12 may, for example, each include three coils, oriented along respective spatial axes. The digitized values of the receiver voltages from the digital converter 14 pass to a digital signal processing system 18 that may be implemented in or may interface with a host processor 20 Values of the transmitter coil drive signals 14 are also digitized by an analog to digital converter, and pass on line 15, to the digital signal processing system 18. In a preferred embodiment, the driver 11 applies known or approximately known voltages, rather than known or approximately known currents, to the transmitter assembly 10, and measures one or more currents induced in the coils of the transmitter assembly. This voltage-driven approach advantageously alleviates the need to control the phase of one or more currents applied to the transmitter coils, and further permits the system to function even with mistuned and/or non-orthogonal transmitter coils. Those having ordinary skill in the art will appreciate that the transmitter in a system according to the teachings of the invention can also be driven by currents rather than voltages.

The various signals are transmitted, sampled, and combined and processed in coordination, for which operation a timing and synchronization control unit 30 forms a number of basic synchronized timing signals to define or control, for example, the multiplexing of signals between the transmission and receiving coils, control timing of the digitizing circuits, control the analog-to-digital (ADC) sampling rate, and the processing of the digitized raw signals from the coils to produce a processed raw data output. The host processor also operates with the raw data to effect the computational algorithms for determining coordinates and correcting position and orientation determinations.

Figure 2:
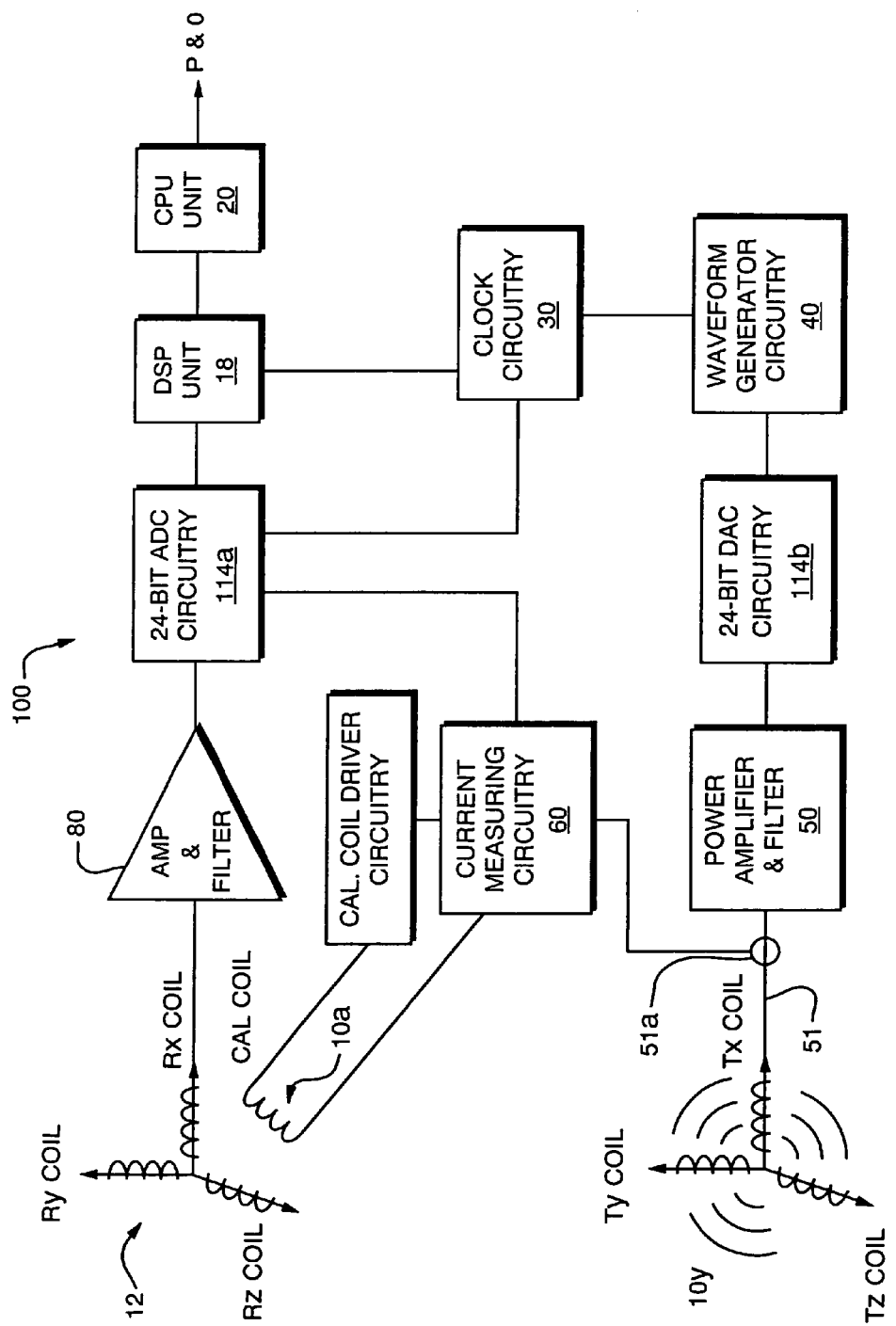
FIG. 2 is a hardware block diagram of a preferred embodiment.

FIG. 2 shows a more detailed hardware block diagram of this aspect of a tracking system which, in accordance with the present invention, is configured to make a robust and accurate determination of mutual inductance of the various transmitter and receiver assembly coil pairs. That information is then applied as further described below to determine the position and orientation coordinates of one assembly with respect to the other. For simplicity, the same numerals as employed in FIG. 1 are used to designate the transmitter, receiver, host processor, digital signal processor and synchronization or control circuitry.

As shown in this embodiment, a clock generator circuit 30 provides timing signals which are applied to different units for effecting synchronized processing described further below. These units include a signal sampling analog-to-digital converter 114a (sometimes referred to as ADC 114 or simply an A/D unit, below), which digitizes the signal values received from the receiver assembly and the drive signal values sampled from the transmitter assembly; a digital-to-analog converter (DAC) 114b which converts digital drive waveform signals to analog voltages for powering the amplifier which supplies transmitter drive signals; and a digital signal processing unit 18 and wave form generator 40.

The wave form generator 40 is a digital frequency synthesizer that generates digital values of a sine wave signal at one or more selected frequencies. These may include, for example, a separate frequency for driving each of the transmitter coils. These digital values are converted to analog values by DAC 114b, and are fed to a power amplifier and filter 50 for driving each transmitter coil. Advantageously, the power amplifier may be a voltage amplifier. The drive signal at any given time, is switched by a current multiplexer to the appropriate coil, and simultaneously the induced voltages in the receiving coils are demodulated at the frequency of the transmitted drive signal. Meanwhile, the drive current to the transmitter assembly is detected by a current sensor 51a and is measured by current measuring circuitry 60.

As further shown in FIG. 2, the receiver coil assembly includes a calibration transmitting coil 10a fixed at a position close to the three receiver coils of the assembly. Coil 10a may be, for example, immovably secured in a fixed orientation relative to the three receiver coils in an integrated unit. The coil 10a is operated to generate a local magnetic field, oriented so that it induces calibration voltage signals in each of the receiving coils. The drive current in this coil is also measured by the current measuring circuitry 60. Coil 10a is energized, as described further below in connection with determination of mutual inductances, to effect normalization of the component signals received in the three receiving coils $R_x$, $R_y$, $R_z$. The calibration coil 10a is driven by a calibration coil driver.

The receiver coils $R_x$, $R_y$, $R_z$ provide their voltage outputs to a preamp and filter 80, the output of which is fed to the analog-to-digital converter ADC 114a, as described above, to produce digital signal values for processing. Converter 114a also receives as an input, the outputs of the current measuring circuitry 60, so that the ADC 114a provides digital values of both the calibration coil current and the transmitter coil currents to the digital signal processing unit 18. Coordination between the various transmitting, receiving, sensing and converting steps is carried out with timing signals from the clock generator circuitry 30. By way of example, clock circuitry 30 may operate with a 25 megahertz clock, dividing it down (e.g., by 256) to set an ADC sample rate of 97.65625 kilohertz, which is successively divided by 2, by 1440, and by 256 to provide sample rate framing signals of 48.828125 kilohertz for the DAC, and end of cycle frame signal at 33.90842 Hz for a sum of products (SOP) processing module implemented in the signal processor DSP 18. Further frequency division may provide a current multiplexer cycle rate (for switching transmitter drive cycles to different coils) of 0.13245477

Hertz, or other synchronized timing signals as appropriate. Thus, operation of the various hardware units shown in FIG. 2 is synchronized by the clock generator circuit 30. Such an exemplary timing unit is shown in FIG. 5E.

One of the clock signals is fed to a digital wave form generator 40 that synthesizes three distinct drive frequencies for the x-, y- and z-transmitter coils. It will be understood that the digital wave form generator 40 may be implemented in the host processor 20. However, it is preferably a specialized frequency synthesis chip or circuit, which produces a digital continuous sine wave of precise frequency and phase. As described further below, the different frequencies are used to drive independent magnetic field generator coils, and corresponding signals induced in receiver coils are detected and processed in a simple digital demodulator, a sum-of-products processor. Preferably, the synthesized frequencies are integral multiples of the sum of products digital signal processing cycle rates (i.e., the cycle rates of the DSP unit 18) so that the sine wave repeats exactly every SOP cycle with no discontinuity between cycles. The frequencies so generated are fixed, and the sine wave generator may be implemented in a known fashion by precalculating samples of the desired sign wave signals and storing the samples in a programmable read only memory (PROM). The PROM addresses are then driven by signals from timing generating counters (not shown) so that the PROM outputs the samples in the serial format required by the digital-to-analog converter 114b. Another PROM output may implement the divide by 1440 control logic.

The digital output values of generator 40 are converted to a differential analog voltage in the DAC circuitry 114b, which may, for example, be a 24-bit Deltasigma digital-analog-converter. Its output analog signal is amplified by the amplifier 50 which may, for example, be implemented with a low pass filter and a fixed gain differential amplifier.

As is apparent from the circuitry described thus far, systems of the invention set out to measure both the transmitter coil drive currents and the receiver coil induced voltages. These are ratiometrically combined to form mutual inductance measurements. Various further construction details may be practiced in order to have the detected signals represent as accurately as possible the desired positional field dependence. FIGS. 5A–5D illustrate further construction details useful in preferred constructions of the transmitting and receiving hardware.

Figure 5A:
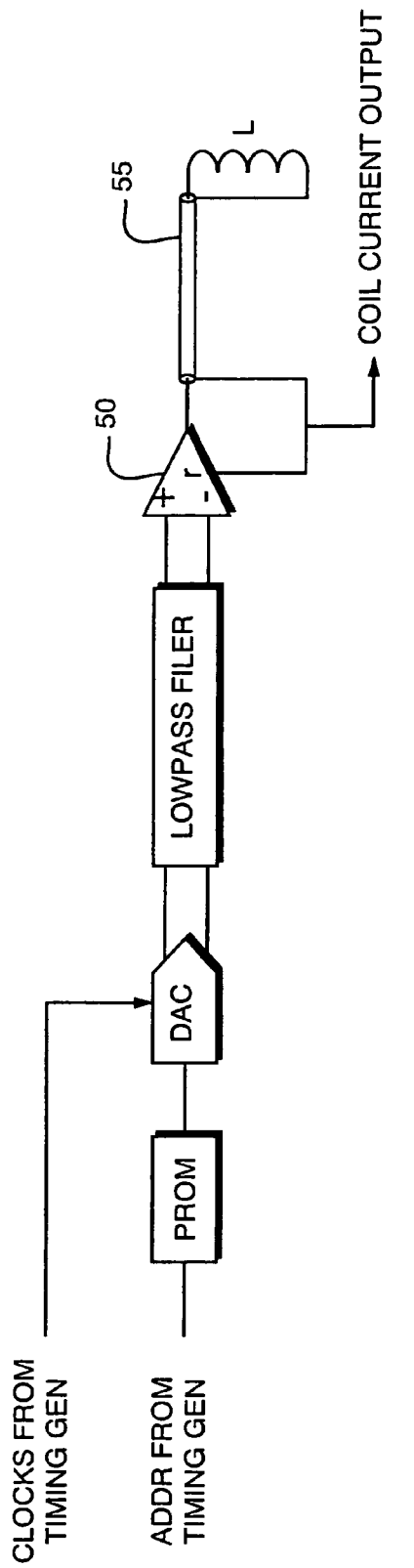

As shown in FIG. 5A, each transmitting coil is driven by a differential amplifier 50 that amplifies the analog-converted synthesized drive frequency signal. The r input of the differential amplifier is connected to the low end of the transmitter coil (denoted L in the Figure), which is also connected to a virtual ground. A coaxial cable 55 carries the drive signal to the high end of the transmitter coil L, thus avoiding introduction of electromagnetic fields due to currents within the drive cable. The virtual ground, although not exactly a ground voltage, is connected to the r input of the amplifier, thus ensuring that the actual voltage applied across the transmitter coil will not be affected by small stray voltages on the virtual ground. In this manner, a stable drive voltage is applied across the transmitter coil.

Further, because the impedance of the amplifier r input is high compared to the impedance of virtual ground or real ground, and its current signal is low, the current drawn through the r connection is substantially less than (e.g., typically $10^4$ times less than) the current through the coil itself. This small error may be estimated and corrected mathematically in subsequent processing. Similarly, the coaxial cable capacitance may shunt a small current around the coil; this current may also be estimated and corrected mathematically.

As further shown in FIG. 5A, as a coil is driven by the amplifier 50, the coil current is sampled between the low end of the coil and the r terminal of the driving amplifier. The detected drive current is applied together with induced receiver coil signals for the computation of mutual inductance.

Figure 5B:
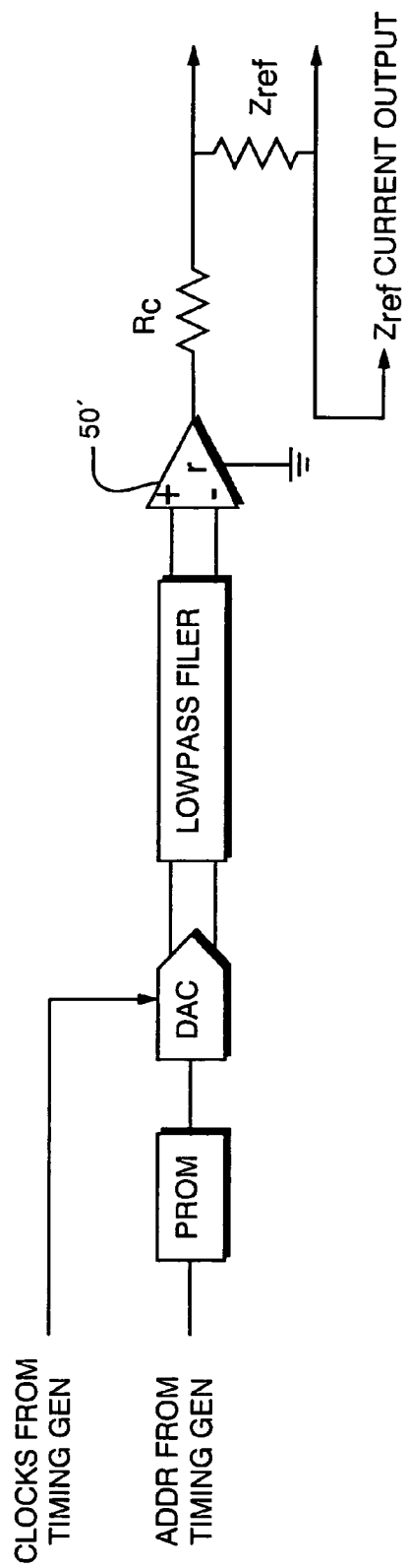

In addition, as shown in FIG. 5B, a reference impedance measurement is also provided at the transmitter by having a defined drive signal periodically switched through a reference impedance $Z_{ref}$. The impedance of $Z_{ref}$ is much larger than the coil to coil mutual impedances, so the $Z_{ref}$ driver provides a smaller current. As seen in FIG. 5B, a resistor, $R_c$, which is large compared to $Z_{ref}$, converts the voltage output of the difference amplifier 50' to a small current in $Z_{ref}$. This connection, viz., the difference amplifier input r, is grounded, rather than connected to the low end of $Z_{ref}$, for two reasons. First, the input r draws a small current which is significant compared to the current in $Z_{ref}$. Second, the receiver measurement channel responses to $Z_{ref}$ are measured only when the current through $Z_{ref}$ is being measured by the current-measurement channel. The reference impedance $Z_{ref}$ may plug directly onto the connectors on the receiver electronics board thus avoiding the introduction of artifacts or the parasitic characteristics of cabling. In this embodiment, $Z_{ref}$ is utilized only for determining the mutual inductances $L_{cal}$ between the calibration transmitting coil 10a (FIG. 2) and the receiver coils at the time of manufacturing the receiver assembly. While tracking, the three $L_{cal}$ values corresponding to mutual inductances between the calibration transmitting coil 10a and each of the three receiver coils are employed as mutual inductance standards.

The overall arrangement of the transmitter section is shown in FIG. 5C. The driver/amplifier 50 is connected in turn to each of the coils and referenced by a current-switching multiplexer (CMX) 60. The virtual grounds for all the transmitter coils go through a current-mode switch matrix, that connects none or one transmitter coil current to the primary winding (e.g., a single-turn primary) of a current transformer $T_c$ while connecting all the remaining transmitter coils to the high-current transmitter-coil common-ground point t. The selected current thus goes through the primary of the current transformer $T_c$ to the ground point t. A suitable current transformer $T_c$ may have a primary-to-secondary turns ratio of about 1:200. It operates to isolate the large transmitter currents from analog ground of the receiver electronics, accurately reducing the transmitter currents to values within the range of the virtual-ground preamp, and minimizing the reflected virtual-ground impedance seen by the transmitter coils.

The mutual-impedance reference is preferably operated at a lower current than the transmitter coils are operated, so the mutual-impedance-reference current is switched in or out (as shown) on the secondary side of the current transformer $T_c$. Moreover, the secondary of $T_c$ is always in the circuit, to cancel effects due to transformer magnetizing current, so that the magnetizing current then appears as just another constant complex gain error in the current-measurement channel. Such constant gain errors cancel out in data-reduction calculations. In FIG. 5C, the op amp and resistor $R_f$ form a virtual-ground current-input, voltage-output amplifier.

Figure 5D:
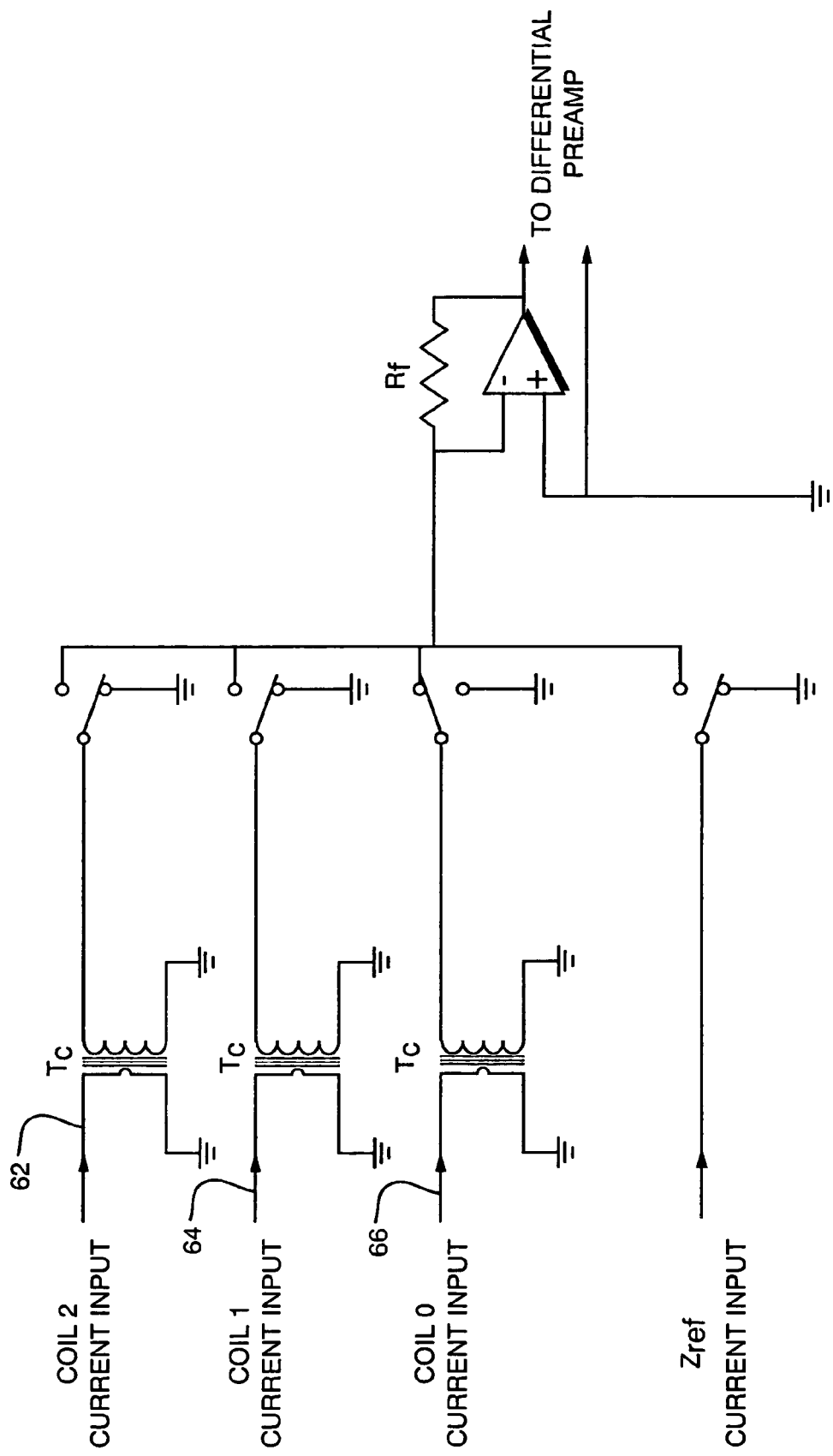
Figure 5E:
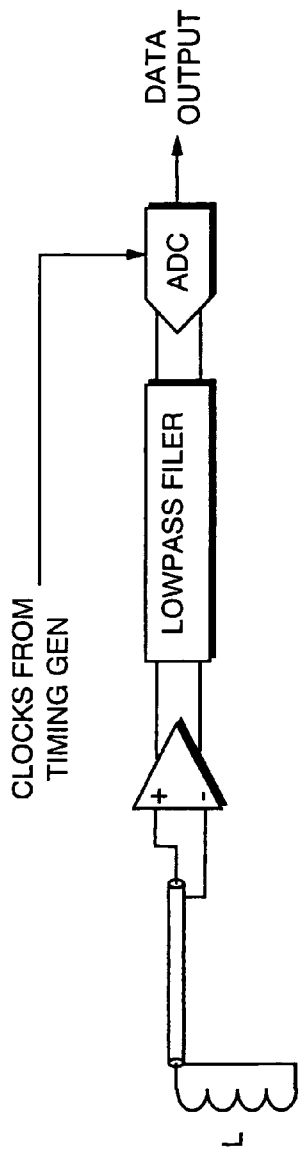

FIG. 5D provides an arrangement alternative to that shown in FIG. 5C. In this alternative arrangement, three transformers (62, 64, 66) are utilized, and the current switches are connected to the secondary windings of the transformers. The impedance variation seen by each transformer coil in the transformer primary circuit, as a result of opening and closing the corresponding switch, is much lower than the variation seen in the arrangement of FIG. 5C. In particular, the variations are reduced by a factor equal to the square of the transformer turns ratio. For example, the use of a turns ratio of 1:200 in the arrangement of FIG. 5D results in reducing the impedance variations by a factor of 40,000 relative to that in the arrangement of FIG. 5C.

In operation of the system, magnetic fields generated by the transmitter coils induce voltage signals in the receiver coils, and these are received and sampled to develop raw received signal values for the processing. The voltage-input preamp and ADC channel for one receiver coil L is shown in FIG. 5E. The voltage from the inductor L is applied via a coaxial cable 55 to the differential-voltage-input preamp. The preamp output is applied to the input of an analog to digital converter, such as the above described 24-bit Delta-sigma ADC, through a passive lowpass filter. The filter eliminates alias responses as well as effects due to nonlinear ADC input currents. Use of a coaxial cable has the advantageous benefit that external electromagnetic fields can induce no potentials between the center conductor and the shield of the coaxial cable (assuming a perfectly-conducting shield). By contrast, a conventional twisted-pair cable may cancel effects due to uniform applied electromagnetic fields, but can introduce extraneous signals in the presence of gradient fields (such as spatially varying fields) are used in the system.

Thus, in the illustrated embodiment, there is one voltage input channel for each receiver coil, and a channel for the current preamp.

Figure 3:
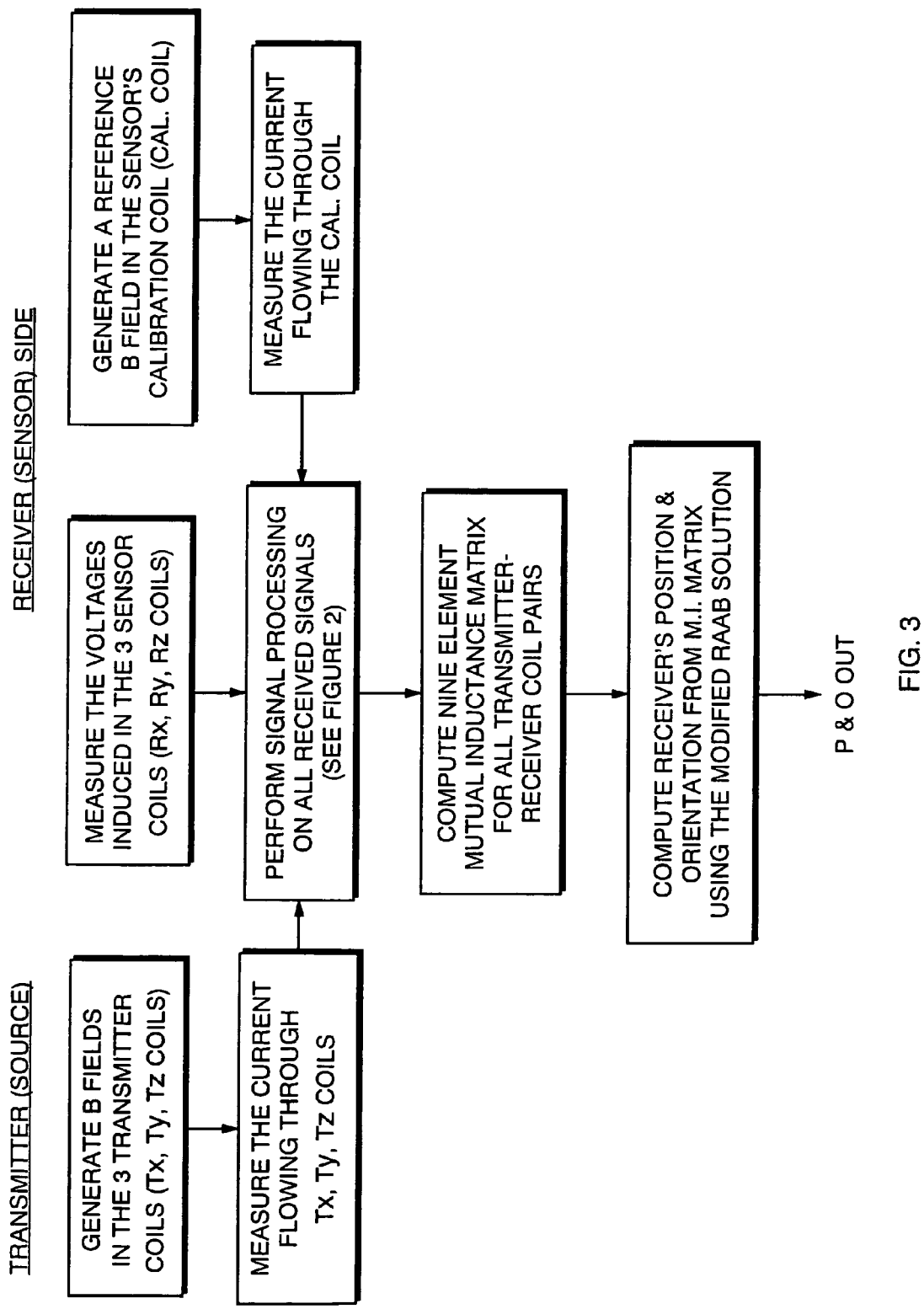
FIG. 3 is a high level flow chart illustrating operation of a system according to one aspect of the invention.

Overall operation 200 of the position sensing system proceeds as shown in FIG. 3. The transmitting x-, y- and z-coils $T_x$, $T_y$, $T_z$ are driven to generate magnetic fields, and the voltages induced in the three sensor receiver coils denoted $R_x$, $R_y$, $R_z$ are measured. In addition, a reference magnetic field is generated in a calibration coil 10a coil fixed in or close to the receiving coil assembly. The currents flowing through the transmitting coils and the current flowing through the calibration coil are each measured, and all the signals, including the received voltage signals in each receiver coil, are digitized and passed to a signal processing unit described below more fully in connection with FIG. 4. The ADC sampling is controlled by a common timing generator so that the timing relationship between ADC samples and DAC samples is tightly controlled. A suitable timing module is shown in FIG. 5F, having the representative framing, cycle time and other processing or sampling intervals described above. The ADC outputs, and timing reference information from the timing generator pass to a digital signal processing system. The signal processing applies quadrature demodulation (i.e., digital heterodyning at the driving frequency of the currently-actuated transmitting x-, y-, z- or calibration coil signal) to accumulate sum-of-products (SOP) complex raw signal values, and computes various matrices which allow one to normalize the coupling between the coils and the response of the receiver coils to the calibration coil.

These are used in the next stage to form a nine element mutual inductance matrix for all of the (3) transmitter and (3) receiver coil pairs. The matrix is then used to compute coordinates of the receiver coil assembly with respect to the transmitter. The overall approach for the latter computation may be similar to that employed in a conventional field model dipole approach, such as that described in the 1979 paper of F. H. Raab et al. Volume AES-15, No. 5, pp. 709–718, and Frederick H. Raab. *Quasi-static Magnetic Field Technique for Determining Position and Orientation. IEEE Transactions on Geoscience and Remote* Sensing. GE-19 (4): 235–243, October 1981. For computation of position and orientation coordinates, the processing preferably proceeds by starting with an initial estimate of the six position and orientation coordinates, applying those coordinates to compute a mutual inductance matrix, and iteratively refining the coordinate estimate to enhance the goodness of fit between the mutual inductance values as measured, and those predicted from the estimate.

As discussed further below, various features of the processing make the mutual inductance model highly accurate and not prone to errors of scale or position. Moreover since direct solutions are possible, the iteration proceeds quickly so that the position and orientation coordinates may be output based on the estimated coordinates and measured mutual inductance matrix. Appendix A attached hereto illustrates a suitable calculation for deriving an initial set of position and orientation coordinates from a measured set of dipole-modeled mutual inductances $L_{tr}$ of the transmitter/ receiver coil pairs. The dimensions of the coils are assumed to be small compared to their separation, allowing derivation, for example, as described in the paper of Frederick H. Raab. *Quasi-static Magnetic Field Technique for Determining Position and Orientation.* IEEE Transactions on Geoscience and Remote Sensing. GE-19 (4): 235–243, October 1981. Mutual inductances may be calculated for dipole coils or for circuits comprised of straight line segments as outlined in Appendix B and Appendix C. Each of the foregoing appendices is hereby incorporated herein by reference and made a part of this description.

Figure 4:
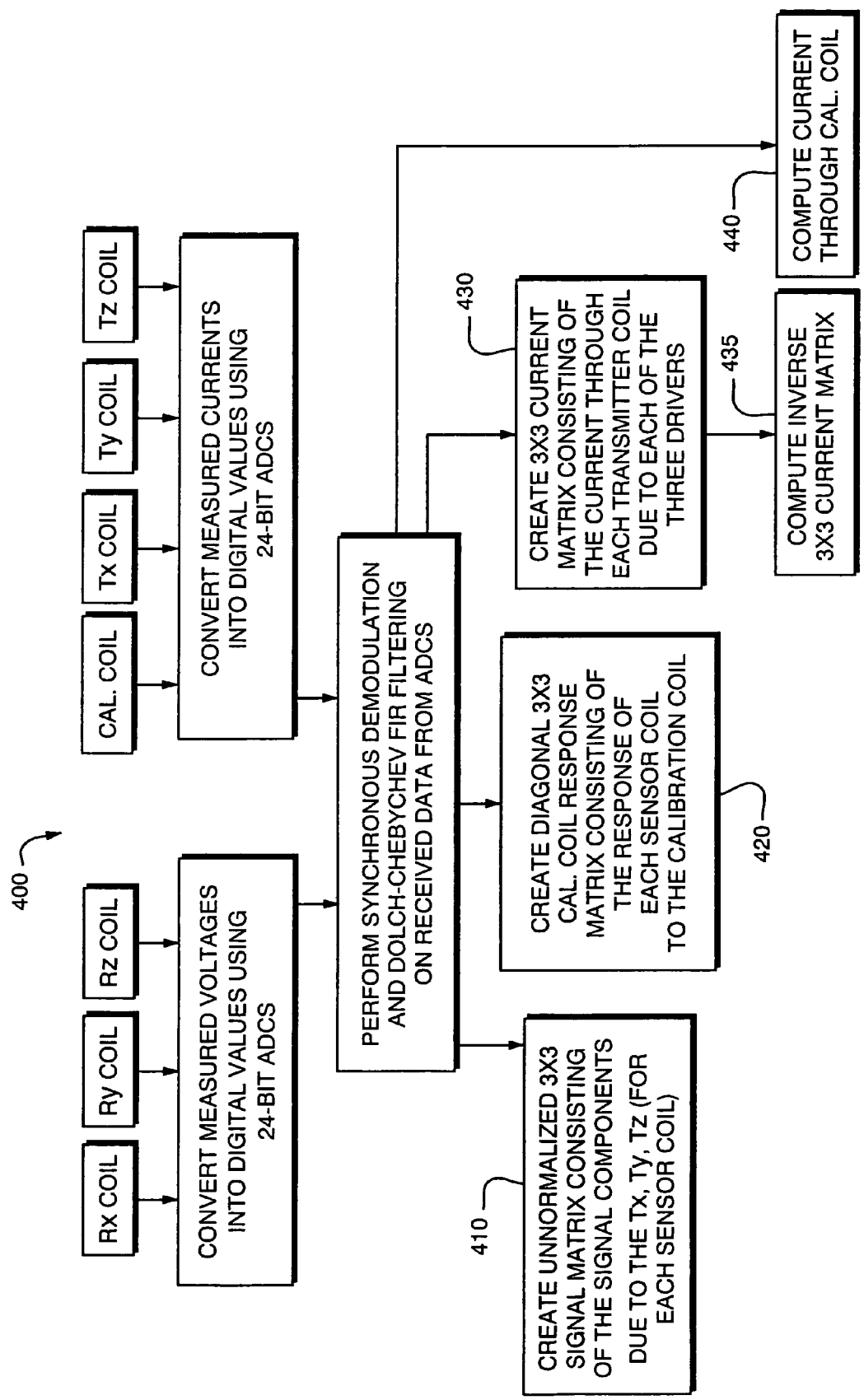
FIG. 4 illustrates signal processing for determining coordinates with the system of FIG. 3.
Figure 5F:
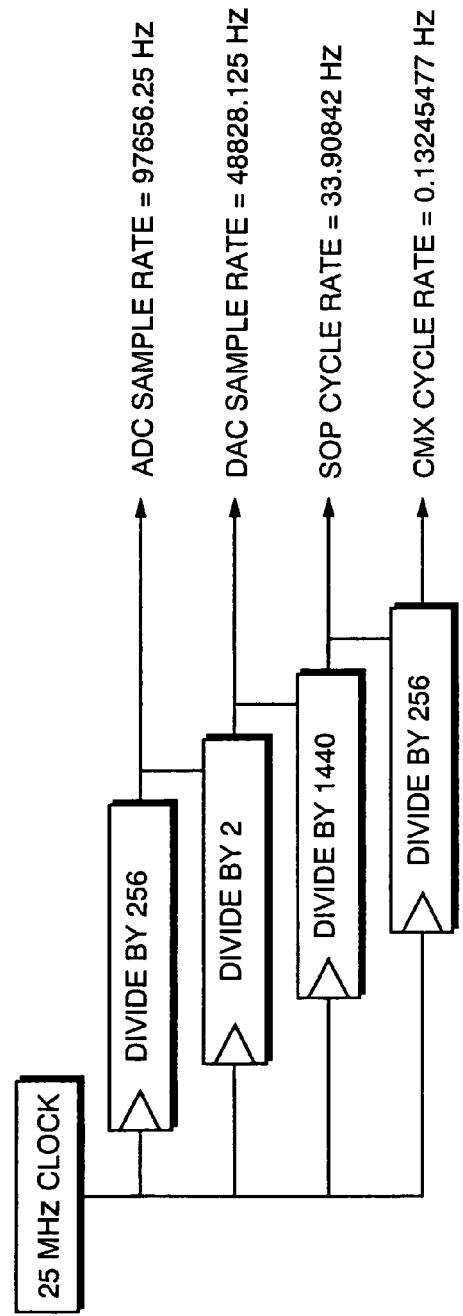

FIG. 4 is a block diagram showing the digital signal processing 400 undertaken with the digitized coil drive current and sensing voltage measurements. As shown, each of the signal measurements is digitized in a high precision (24 bit) ADC. The signals are filtered and synchronously quadrature demodulated, for example, using a Dolch-Chebyshev FIR filter, and the complex signal values are then applied to construct three matrices 410, 420, 430 which are used to determine the mutual inductances and to normalize measurements. Matrix 410 is a raw signal matrix made of the signal components induced in each of the receiver coils by each of the transmitter coils. Matrix 420 is a 3×3 diagonal matrix, the three entries of which represent the response of the respective receiver coils to the calibration coil. Matrix 430 is a 3×3 current matrix with entries representing the current through each coil (on the diagonal) and the current due to the other coils (off the diagonal). That is, it is a cross-coupling matrix. The DSP or processor also computes the inverse 435 of this matrix, and the current through the calibration coil is provided as a separate parameter 440.

In general, the mutual impedance measuring system is designed for measurement of small mutual impedances at frequencies between 100 Hz and 40 kHz, and preferably between about 10 kHz and 15 kHz. The reference impedance $Z_{ref}$ may be a 10 ohm ±100 ppm four-terminal resistor, so that $Z_{ref}$ is real and independent of frequency at the frequencies of interest. The whole system is ratiometric: the mutual impedances are measured with respect to $Z_{ref}$ so that no precision voltage or current references are required. Moreover, the frequency responses of the receiver measuring channel and the current measuring channel are the same, so that factors of the complex gains that vary with frequency will cancel in the ratioing process. Similarly, frequency-independent complex gain factors of the receiver measuring channels will also cancel in the determining the ratio of mutual impedances to $Z_{ref}$.

Overall, the system operates by converting the raw signal measurements as discussed above to a mutual inductance matrix, and then solving for position and orientation (P&O) from the mutual inductance.

The first step to computing P&O is converting sum-of-products (SOP) data into a normalized raw signal matrix (RSM) of mutual inductances. The SOP data is processed to preserve phase information, so there is a real and an imaginary component of each parameter. The unnormalized matrix has these complex entries, while, the mutual inductance matrix consists solely of real numbers. As discussed above, it is the end result of normalizing a complex signal matrix (CSM) for the effects of current, coil and calibration coil response. The goal of this step is to end up with a 3×3 matrix containing the mutual inductances between all possible combinations of sensor and transmitter coils. Because there are three sensor and three transmitter coils, there are a total of nine elements in the signal matrix. Each row of the matrix corresponds to a sensor coil and each column to a transmitter coil.

The RSM is computed by performing a series of matrix multiplication operations.

The effects of transmitter current are normalized out (because the B field is directly proportional to the current through the transmitter), as are the effects of frequency (db/dt) and receiver channel gain (using the calibration coil response matrices). The formula is shown below:

inverse of the transmitter gain matrix. Detailed mathematical derivation of this method is given in the attached Appendix A.

Specifically, $$R = (Recr\_gain\_matrix) * RSM * (Trans\_gain\_matrix^{-1})$$

where R is now a 3×3 matrix where the effects of receiver and transmitter gain and non-orthogonalities have been removed. One can now estimate the range, r, (the square root of $x^2+y^2+z^2$) and the magnitude of the x,y,z coordinates based on the square of the total field from the three transmitter coils.

The pertinent equations (1–4) are:

$$r = \sqrt[6]{6.0 * k^2 / Stotal} \quad (1)$$

$$x = r^4/k * \sqrt{(5.0 * Sx - Sy - Sz)/18} \quad (2)$$

$$y = r^4/k * \sqrt{(5.0 * Sy - Sx - Sz)/18} \quad (3)$$

$$z = r^4/k * \sqrt{(5.0 * Sz - Sy - Sx)/18} \quad (4)$$

where, k is a scale factor that is the product of the area and number of turns of receiver and transmitter coils and permeability of free space. Stotal is the sum of signal matrix elements squared. Sx, Sy, Sz, are the sum of signal matrix elements squared for the X,Y,Z transmitter coils, respectively.

Because of the hemispherical ambiguity associated with the tracker, the processor may always assume it is operating $$RSM \text{ (the mutual inductance matrix) equals } ICM * \begin{pmatrix} (Fcal/F0) & 0 & 0 \\ 0 & Fcal/F1 & 0 \\ 0 & 0 & Fcal/F2 \end{pmatrix} * CSM *$$

$$\begin{pmatrix} Fcal\_sop\_C/Facl\_sop\_0 & 0 & 0 \\ 0 & Fcal\_sop\_C/Fcal\_sop\_1 & 0 \\ 0 & 0 & Fcal\_sop\_C/Fcal\_sop\_2 \end{pmatrix} *$$

$$\begin{pmatrix} cc\_cf[0] & 0 & 0 \\ 0 & cc\_cf[1] & 0 \\ 0 & 0 & cc\_cf[2] \end{pmatrix}$$

where F0, F1, F2 are the frequencies of the x-, y- and z-transmitter coils, and where the complex entry Fcal_sop_C is the measured sum-of-products current through the calibration coil, Fcal_sop_0 is the response of the x-sensor coil to the calibration coil field, etc.

The above mutual inductance matrix is then applied to determine the position and orientation coordinates of the coil assembly. This operation proceeds by first obtaining a good estimate of P&O, for example, by using the direct dipole solution of the Raab paper cited above (which may be augmented to correct for coil size and known field disturbances). The processor first factors out the effects of gain & non-orthogonality of both the receiver and transmitter coils. This may be done by pre-multiplying the RSM by the receiver gain matrix inverse, and post-multiplying by the in the +X hemisphere, and simply take dot products between sensor output vectors (the rows in a transposed signal matrix) to determine the sign of y and z.

However, the solution is unstable if any of the coordinate values is close to zero. (See Appendix A). To correct for this, the processor preferably mathematically rotates the signal matrix elements to move the solution into an optimal (non-zero) region which herein refers to a region in which the numerical coordinate values are substantially non-vanishing such that a stable solution of the coordinate values can be obtained by utilizing the above methodology The rotation is determined by computing the quaternion effective to move the initial position estimate to an "ideal" solution location where x=y=z (i.e., away from the x, y and z axes). This ensures that the solution is numerically accurate and stable. The processor then recalculates equations (1)–(4) with the rotated R matrix. After determining these "rotated" position coordinates, the processor de-rotates with the inverse quaternion to obtain a better estimate of the true position. Again, dot products are employed to determine the sign of the coordinates.

The r, x, y and z values are then used to compute 3×3 matrices $T\alpha$, $T\beta$ and their inverses. The matrices $T\alpha$, $T\beta$ are rotation matrices built from the (positional) spherical coordinates angles, $\alpha$, $\beta$, respectively. Note, however, that because $$\cos(\alpha)=x/sqrt(x^2+y^2)$$

$$\sin(\beta)=z/r$$

$T\alpha$, $T\beta$ and their inverses ($T\alpha^{-1}$, $T\beta^{-1}$) may be constructed directly from x,y, and z. These matrices along with the inverse of a constant sensitivity matrix, $S^{-1}$, allow the inverse-coupling matrix, $Q^{-1}$ (described in the aforesaid Raab paper) to be computed.

Basically, $$Q^{-1}=T\alpha^{-1}*T\beta^{-1}*S^{-1}*T\beta*T\alpha \qquad (5)$$

With $Q^{-1}$ and the signal matrix, R, the processor computes the rotation matrix, A, that converts a zero-orientation sensor output into the output of the true sensor:

$$A=(r^3/k)*R*Q^{-1} \qquad (6)$$

where the elements of A can be described by a rotation quaternion, q={qs,qx,qy,qz}:

$$A[0][0]=(qs^2+qx^2-qz^2),$$

$$A[0][1]=2*(qy*qx+qs*qz),$$

$$A[0][2]=2*(qz*qx-qs*qy),$$

$$A[1][0]=2*(qy*qx-qs*qz),$$

$$A[1][1]=(qs^2-qx^2+qy^2-qz^2),$$

$$A[1][2]=2*(qz*qy+qs*qx),$$

$$A[2][0]=2*(qz*qx+qs*qy),$$

$$A[2][1]=2*(qz*qy-qs*qx),$$

$$A[2][2]=(qs^2-qx^2+qy^2+qz^2)$$

The elements of A may be used to find a rotation quaternion, 'q', using the procedure in Appendix A8 of the paper of B. Horn, *Closed-form solution of absolute orientation using unit quaternions*, J. Opt Soc. Amer. Vol 4. p 629, April, 1987. Note, however, that here A is the inverse of the rotation matrix described in that paper.

The foregoing procedure provides a very good estimate for the position and orientation of the sensor. To refine the estimate of position and orientation, the processor next applies a fitting, such as a first-order or least square algorithm, to create a best-fit between a set of model estimated mutual inductances and the measured mutual inductances in the RSM. The idea is to compute a set of small correction values to apply to the estimated P&O. The basic equation is:

$$E+S*(delta\_P\_O\_vector)=R \qquad (7)$$

where

R is the measured signal matrix, formulated as a nine element vector;

E is an estimated signal matrix computed using both the direct solution P&O estimate and a magnetic field model based on the actual geometry of the coils employed in the system (where the signal matrix E is also formulated as a nine element vector);

S is a 9×6 sensitivity matrix which holds the partial derivatives of signal matrix elements with respect to six position and orientation parameters (x,y,z,qx,qy,qz); and delta_P_O vector is the 6 element delta correction vector ($\Delta x$, $\Delta y$, $\Delta z$, $\Delta qx$, $\Delta qy$, $\Delta qz$) that is to be solved for.

The fourth component of the delta quaternion, $\Delta qs$, may be solved for by normalizing it to unit length.

Note that because the matrix S is not square, it cannot be inverted. However, to put it into an invertible form, one can multiply it by its transpose ($S^T$). See, for example, W. Brognan. *Modern Control Theory*. Prentice-Hall, 1991, pp 222–223. The least squares equation we end up with is:

$$delta\_P\_O\_vector=[\Delta x, \Delta y, \Delta z, \Delta qx, \Delta qy, \Delta qz]^T= (S^T*S)^{-1}* (S^T)*(R-E) \qquad (8)$$

Finally, sensor position is adjusted by:

$$x=x+\Delta x; y=y+\Delta y; z=z+\Delta z$$

and the sensor orientation (as a quaternion), qorient, is adjusted by rotating it by the computed delta quaternion, qdelta:

qoyient=qdelta*qodent

Thus, the processor operating with SOP data from the magnetic tracking units computes and refine the position and orientation of the movable coil assembly.

As noted above, certain structures present in the tracking arena may introduce field distortions because eddy currents induced in conductive structures will themselves generate magnetic fields. In accordance with other aspects of the invention, this problem is addressed in one or more of several ways.

One of these ways is to mount the receiver (sensor) of the system on or close to a major interfering structure, such as (in a medical context) the C arm of a fluoroscope assembly. The transmitter coil assembly is then the movable assembly of the tracker, and will thus be generally positioned remotely from the interfering structure. The mutual inductance tracker of the invention can be configured to operate effectively with small coils which may be carried by a hand-held tool and the like, thereby rendering the above approach feasible. Further, the use of mutual inductance between the transmitter and receiver units in the electromagnetic tracker of the invention allows swapping the functionality of the transmitter and receiver units, e.g., utilizing a nominal sensor coil as a transmitter and/or a nominal transmitter coil as a receiver. This reciprocity can be particularly advantageous because, in some cases, it may be more convenient to map and/or model the field generated by one unit, e.g., receiver, rather than the other, e.g., transmitter.

Another aspect of the invention dealing with the field disturbance problem is to mount a standardized conductor about such an interfering structure to operate as a shield (e.g., with respect to disturbances originating within the shield) and a known disturber, as seen by a sensor positioned outside the shield. The standardized conductor, such as a metal can, then has a fixed position relative to one of the coil assemblies, and may be effectively modeled. Thus, the eddy currents induced in the sheet metal cylinder by the magnetic field from the transmitter assembly, and the secondary B field formed by these induced currents, may be modeled such that the processor can apply determinable field contributions from the shield. Without such a shield, applicant has found that when a coil assembly is employed in proximity to certain interfering structures (such as the imaging assembly of a fluoroscope), the disturbance caused by that structure may vary considerably for two different but apparently identical units. The shield moderates such differences; electromagnetic fields originating within the shield are largely null outside the shield. Moreover, little of the tracking signal origination outside the shield penetrates inside, so that the level of eddy currents induced in the structural conductive elements inside the shield are subject only to quite low fields and their eddy currents and secondary field effects are greatly diminished. These combined effects allow a tracking system to operate effectively by applying standardized (modeled or calibrated) corrections for the shield alone, without regard to the specific structure (such as a fluoroscope imaging assembly) that it isolates.

Preferably, the shield is made of a single piece of a highly conducting material, e.g., a metal such as silver, copper or aluminum, or a conductive composite. The shield surrounds the targeted component or piece of interfering equipment, such as the image intensifier assembly of a fluoroscope, as much as possible, consistent with system constraints (e.g., X-ray transparency of the top end, mechanical protrusion limits for camera movement, etc.). Preferably, the shield thickness is sufficient, e.g., more than the skin depth of the metal or more than several skin depths, so that the magnetic field it generates will not appreciably penetrate the shield or extend into the volume behind the shield.

The field distortions introduced by the shield may be mapped and a tracker-correction table may be generated in a preliminary set-up or calibration step, or the effect of the shield may be modeled.

The shield greatly reduces the magnitude of equipment-related magnetic field distortion reaching the targeted structure, and introduces its own, highly determined effects. Thus, as applied, for example to a fluoroscope, changing the image intensifier has no appreciable effect on the resulting field distortion, and one field distortion correction table can be used for all image intensifiers of a given model, and sometimes even for image intensifiers of different models.

Figure 6:
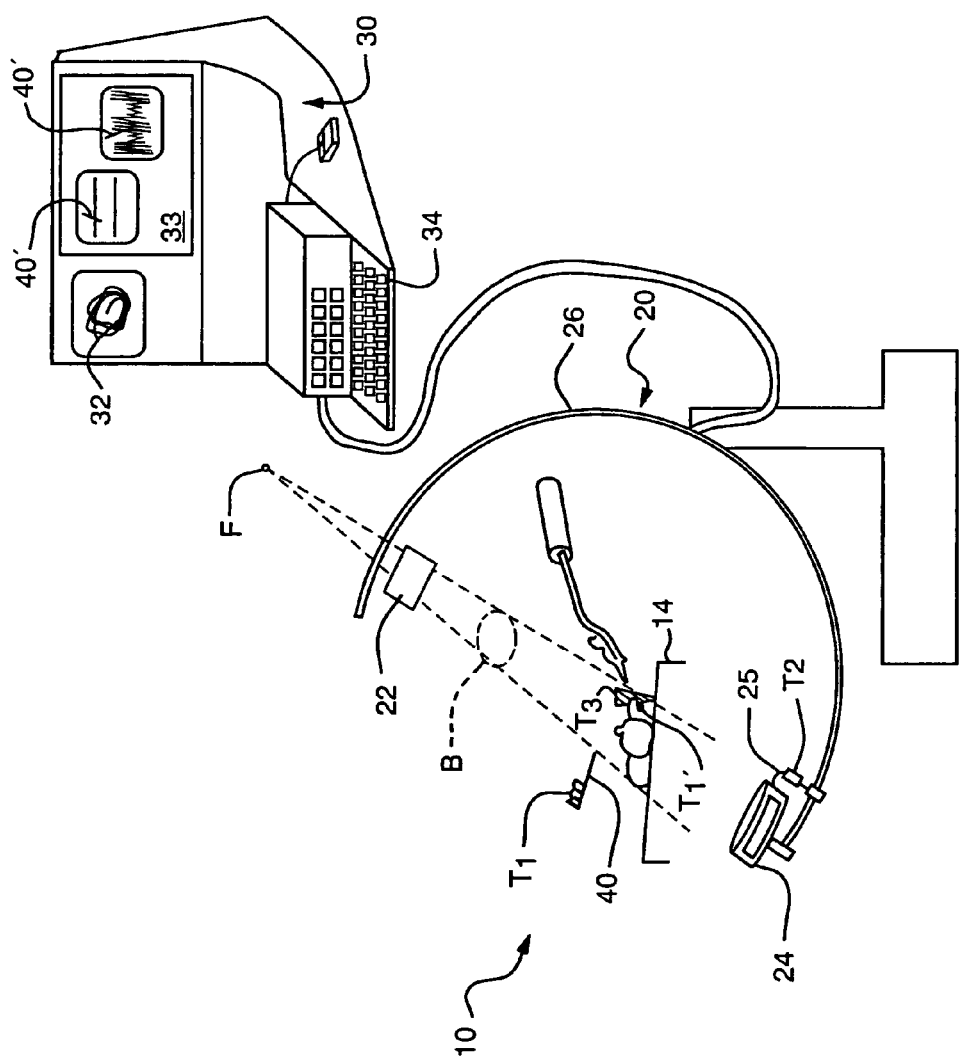
FIG. 6 illustrates aspects of distortion correction in accordance with other aspects of the invention.

FIG. 6 illustrates such a system in an embodiment 10 for use in surgical navigation in an operating room environment As shown, the system 10 includes a fluoroscope 20, a work station 30 having one or more displays 32, 33 and a keyboard/mouse or other user interface 34, and a plurality of tracking elements T1, T2, T3. The displays may illustrate imaged views or synthesized views 40' of tool trajectories, tissue or the like. The fluoroscope 20 is illustrated as a C-arm fluoroscope in which an x-ray source 22 is mounted on a structural member or C-arm 26 opposite to an x-ray receiving and detecting unit, referred to herein as an imaging assembly 24. The C-arm moves about a patient for producing two dimensional projection images of the patient from different angles. The patient remains positioned between the source and the imaging assembly 24, and may, for example, be situated on a table 14 or other support.

The patient may be secured in a fixed position on the support and the support may be tracked, or more typically, the patient may be movably positioned. In the latter case, tracking elements T3 may be affixed to one or more relevant portions of the patient's body. In the illustrated system, tracking elements are mounted such that one element T1 is affixed to, incorporated in or otherwise secured against movement with respect to a surgical tool or probe 40. A second tracking unit T2 is fixed on or in relation to the fluoroscope 20, and a third tracking unit T3 is shown fixed on or in relation to the patient.

The surgical tool may be a rigid probe as shown in FIG. 6, allowing the tracker T1 to be fixed at any known or convenient position, such as on its handle, or the tool may be a flexible tool, such as a catheter, flexible endoscope or an articulated tool. In the latter cases, the tracker T1 is preferably a small, localized element positioned in or at the operative tip of the tool as shown by catheter tracker T1' in FIG. 6, to track coordinates of the tip within the body of the patient.

As will be understood by those having ordinary skill in the art, fluoroscopes typically operate with the x-ray source 22 positioned opposite the camera or image sensing assembly 24. While in some systems, the X-ray source is fixed overhead, and the camera is located below a patient support, the discussion below will be illustrated with regard to the more complex case of a typical C-arm fluoroscope, in which the source and camera are connected by a structural member, the C-arm 26, that allows movement of the source and camera assembly about the patient so it may be positioned to produce x-ray views from different angles or perspectives. In these devices, the imaging beam generally diverges at an angle, the relative locations and orientations of the source and camera vary with position due to structural flexing and mechanical looseness, and the position of both the source and the camera with respect to the patient and/or a tool which it is desired to track may all vary in different shots. Thus, the use of one or more tracking elements T3 (transmitters or receivers) on the structure itself may be useful to quantify these movements in the surgical navigation system. Further details of this complex imaging environment may be found in commonly owned U.S. patent application Ser. Nos. 09/560,940 and 09/560,608, both filed on Apr. 28, 2000, each of which is incorporated herein by reference. Each of those patent applications discloses a tracking system wherein tracking of the fluoroscope as well as the tool and patient produce image sets and surgical navigation of enhanced accuracy.

The imaging beam illustrated by B in FIG. 6 diverges from the source 22 in a generally truncated conical beam shape, and the C-arm 26 is movable along a generally arcuate path to position the source and camera for imaging from different directions. This generally involves positioning the assembly 24 as close as possible behind the relevant tissue or operating area of the patient, while the C-arm assembly is moved roughly about a targeted imaging center to the desired viewing angle. The C-arm or other beam structure 26 may move eccentrically or translationally to allow better clearance of the patient support table, but generally, the camera assembly 24 is positioned close to site of surgical interest. Because, as noted above, the camera 24 may utilize an image sensing unit that introduces distortions into electromagnetic fields employed for tracking, this complicates the task of tracking, particularly in view of the proximity of the disturber to the tracking sensors positioned on the patient or the surgical tool.

As further shown in FIG. 6, this problem is advantageously addressed by providing a conductive shield/distorter 25 surrounding the image assembly 24, which may be a metal or conductive cylinder. Preferably the top face is open, so as to avoid degrading the X-ray image or contrast detected by the assembly 24. Most preferably, the electromagnetic tracking element T3 is a sensor element, rather than a transmitter, and it is mounted in a fixed position in relation to the shield 25. That is, the tracking element T3 is clamped to the shield 25, or clamped to the C-arm (as illustrated) or to the imaging assembly close to the shield. This device architecture is advantageously used in connection with a processor to achieve enhanced speed and robustness of the tracking coordinates.

As discussed above, in a tracker of the invention, a shield may be modeled in the processor, so that a more accurate model of the magnetic field data is present initially, either obviating or reducing the task of actually mapping the disturbed field measurements. When the processor determines position and orientation components by refining an iterative estimation or fitting procedure, for example wherein the system estimates the coordinates of a transmitter or sensor unit, or the relative coordinates by comparing calculated signal measurements with measured signal values, such modeling may produce faster and less computationally intensive convergence of the fitting procedure. Thus, for example, a cylindrical "can" fitted about the imaging assembly of a fluoroscope may be effectively modeled as a conductive ring or annulus at the defined position. This may produce a kernel or an initial seed solution without resorting to massive stored field calibration tables, or may yield a fast or even closed form calculation of the field distribution for P&O determination. A traditional approach to the design of electromagnetic trackers set forth, for example, in the 1981 paper of F. H. Raab, supra, assumes magnetic dipole field distributions for both the transmitting and sensing coils. This assumption permits an analytic solution for position and orientation coordinates (hereinafter, simply "P&O") based on the measured sensor data. However, in cases where the actual fields deviate from the dipole form, application of a dipole-based algorithm produces distorted P&O estimates. Such deviations occur, for instance, when coil sizes are significant relative to the source-sensor separation distance, or when conducting or magnetic materials are located near the sensors. (The term sensor is used herein to refer to both transmitting and receiving coils unless specifically noted). An analytic solution for P&O is not generally possible for non-dipole field models, so in order to continue to use this formalism in the presence of real fields, a typical approach has been to correct the P&O estimates from the dipole algorithm using a large lookup table containing measured values of the distortion over the working volume, as described in Zachman, G. *Distortion Correction of Magnetic Fields for Position Tracking*. Proc. Computer Graphics Int'l (CGI'97), Jun. 23–27, 1997, Hasselt & Diepenbeek, Belgium.

However, in accordance with another aspect of the present invention, rather than proceeding by creating a distortion map for every application, a system implements a P&O determination based on a more accurate model of the sensor field (for example, modeling the extrinsic distortion) that eliminates the need for a map by curing the distortion problem at its source.

Numerical models (e.g., finite element methods) can be made arbitrarily accurate, but the computational cost for this accuracy may become quite high. As an alternative, a given source may be approximated as a collection of simple shapes for which the fields can be expressed analytically. This approach provides a compromise between accuracy and speed, where the accuracy will be limited by the ability to match the actual geometry with a set of simple shapes, which determine the "basic functions" for the expansion.

This approach has been applied in a further aspect of the invention to a fluoroscopic tracking system where the sensor is mounted close to a large parasitic element, namely the C-arm of a fluoroscope. In this case, a distorter element, for example, in the form of a large metal can is preferably mounted on the C-arm image intensifier to dominate the field distortion. The sensor fields are then modeled as a three-axis dipole located near a filamentary conducting ring. The fields of both a dipole and filamentary ring can be computed analytically (see, for example, Smythe, W R. *Static and Dynamic Electricity*. Hemisphere Publishing, New York, 1989. A composite model of the coupling matrix components can therefore be written as the sum of analytic expressions. The following sections describe the model in detail.

To embed the new field model in the tracker fit routine, one needs a way to compute the coupling matrix between the transmitter and receiver in the presence of the distortion source. To accomplish this, applicant makes two assumptions:

(i) Assume that the transmitting and receiving sensor coils can be modeled as magnetic dipole elements. This assumption allows for a convenient dot product relationship between the field vector and induced voltages, as the coils are assumed to be point sources/receivers.

(ii) Assume that the dominant distorter is the metal can around the image intensifier, and that we can model that can as a simple metal ring. This assumption allows us to use analytic expressions for the magnetic fields radiated by the ring, which are available in the literature (Smythe, supra or Jackson, J D *Classical Electrodynamics*. Wiley, New York, 1975).

Using these assumptions, the development proceeds as follows. First, use network theory to derive an expression for the coupling between the transmitter and receiver in the presence of the ring. This expression contains several mutual and self-inductance terms that we need to compute. Known expressions for the coupling between two dipole elements are used together with the fields generated by a ring to compute the required inductances. Finally, the signal matrix elements can be computed as a function of P&O.

Figure 7:
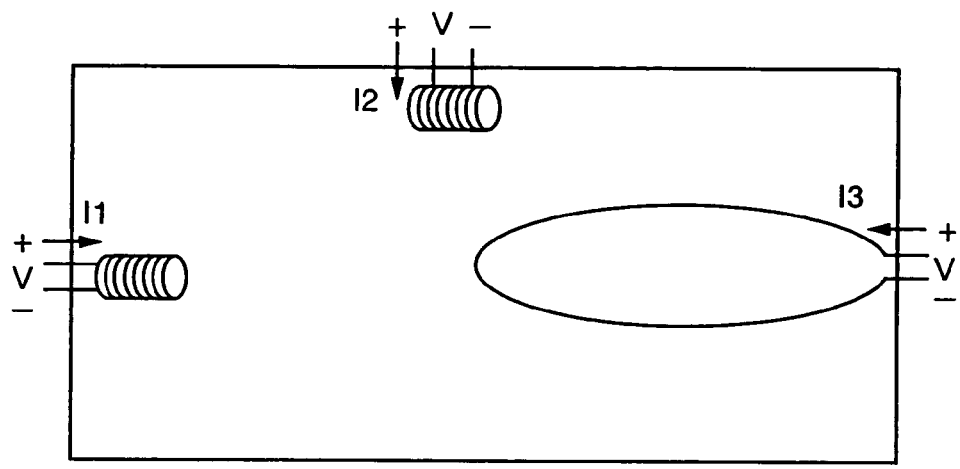
FIG. 7 is a network model of the system of FIG. 6.

The voltage induced on a receive coil due to a current flowing on a transmit coil in the presence of a metal-ring can be computed by considering the system as a three-port network, as schematically shown in FIG. 7.

The impedance parameters describing the coupling among the ports are given by:

$$\begin{bmatrix} V_1 \\ V_2 \\ V_3 \end{bmatrix} = \begin{bmatrix} Z_{11} & Z_{12} & Z_{13} \\ Z_{21} & Z_{22} & Z_{23} \\ Z_{31} & Z_{32} & Z_{33} \end{bmatrix} \cdot \begin{bmatrix} I_1 \\ I_2 \\ I_3 \end{bmatrix}, \text{ where } Z_{ij} = \frac{V_i}{I_j}\bigg|_{I_{k \neq j} = 0}$$

(See, e.g., Pozar, D M. *Microwave Engineering*. Addison-Wesley, Reading, Massachusetts, 1990.)

Consider the case where we want to know the voltage induced on port 2 (the receiver) when port 1 (the transmitter) is driven with a fixed voltage, port 2 is loaded with an impedance Of $Z_L$, and port 3 (the ring) is loaded with a short circuit. After some algebra, we can write the induced voltage on port 2 relative to the current through port I as:

$$\frac{V_2}{I_1} = \left[ j\omega L_{12} - \frac{(j\omega L_{13})(j\omega L_{23})}{Z_{33}} \right] \cdot \left[ 1 + \frac{(j\omega L_{23})^2}{Z_{33} \cdot Z_L} - \frac{Z_{22}}{Z_L} \right]^{-1}. \quad \text{(Eq. 5)}$$

If we assume that $Z_L$ is "large" relative to the other terms in the second set of brackets, and that the resistance of the ring is negligible, Equation 5 reduces to:

$$\frac{V_2}{I_1} \cong j\omega L_{12} - \frac{(j\omega L_{13})(j\omega L_{23})}{L_{33}}$$

This approximation is sufficient for many cases, and the full expression in (5) can be implemented where the additional accuracy is required.

Figure 8:
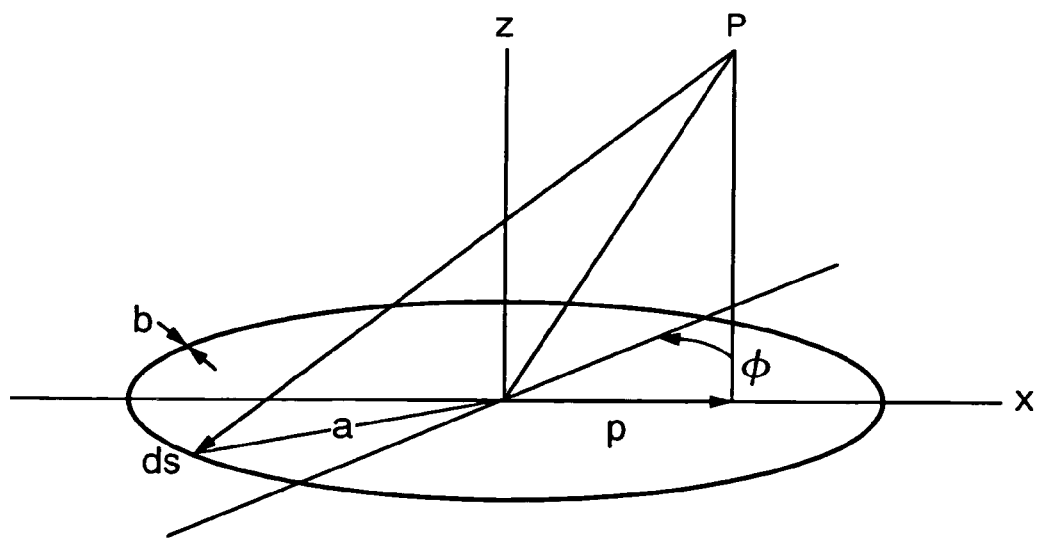
FIG. 8 illustrates geometry of fields for the configuration of FIG. 7.

To calculate the mutual inductance between the transmitting or receiving coils and the ring, we apply reciprocity and let the ring act as the source for both cases. By first calculating the field radiated by a current flowing on the ring, the voltage induced at the transmit or receive coil is given by a simple dot product. Under the magneto-static approximation, the B-field produced by a uniform current I flowing on a filamentary ring (FIG. 8) is given in cylindrical coordinates by Eq. (7):

$$B_\rho = \frac{\mu \cdot I}{2\pi} \cdot \frac{z}{\rho \cdot [(a+\rho)^2 + z^2]^{1/2}} \cdot \left[ -K + \frac{a^2 + \rho^2 + z^2}{(a-\rho)^2 + z^2} \cdot E \right],$$

$$B_z = \frac{\mu \cdot I}{2\pi} \cdot \frac{1}{[(a+\rho)^2 + z^2]^{1/2}} \cdot \left[ -K + \frac{a^2 - \rho^2 - z^2}{(a-\rho)^2 + z^2} \cdot E \right],$$

$$B_\phi = 0,$$

where K and E are complete elliptic integrals of the first and second kind, respectively, and the argument k for the integrals is given by $$4a\rho \cdot [(\alpha+\rho)^2 + z^2]^{-1}.$$

Equation 5 requires the computation of one self inductance term and three mutual inductance terms (additional terms must be calculated for Equation 6, which makes no approximations).

The self-inductance term is for the ring, and is given by [7]

$$L_{ring} = a \cdot \left[ \mu \cdot \left( \ln \frac{8a}{b} - 2 \right) + \frac{1}{4} \mu' \right],$$

where
α is the radius of the loop,
b is the radius of the wire,
μ' is the permeability of the wire material, and
μ is the permeability of free space.

The mutual inductance $L_{12}$ between the transmitting and receiving coils is derived in [10] using the dipole assumption, and can be calculated as $$L_{12} = \frac{\mu_0 A_1 A_2}{4\pi \cdot R^3} \left[ 3 \cdot (\hat{A}_1 \cdot \hat{R}) \cdot (\hat{R} \cdot \hat{A}_2) - (\hat{A}_1 \cdot \hat{A}_2) \right]$$

where
$\overline{A}_1$=effective area of the transmitting dipole,
$\hat{A}_1$=unit vector in the direction of $\overline{A}_1$,
$A_1$=magnitude of $\overline{A}_1$,
$\overline{A}_2$=effective area of the receiving dipole,
$\hat{A}_2$=unit vector in the direction of $\overline{A}_2$,
$A_2$=magnitude of $\overline{A}_2$.
$\overline{R}$=the vector from the transmitter to the receiver
$\hat{R}$=the unit vector in the direction of $\overline{R}$
R=the magnitude of $\overline{R}$.

Given a position and orientation of the sensor relative to the transmitter, the range R can be calculated. The effective area terms are calculated based on the coil geometry and a calibration procedure [11].

The remaining two mutual inductance terms, those between the transmitting coil and the ring, and between the receiving coil and the ring, may be calculated in a similar manner.

The position and orientation of the ring relative to the sensor coils is assumed to be known and fixed. Therefore, to compute the mutual inductance $L_{23}$ in Equation 6, first compute the P&O of the sensor in the coordinate frame of the ring shown in FIG. 8. Next, compute the magnetic field per unit current produced by the ring at the sensor location. Finally, the mutual inductance term is calculated for each sensor coil by taking the dot product between the coil vector and the field, using the point source property of the dipole approximation.

Computing the mutual inductance between the transmitter and the ring requires one additional step. Given the P&O of the sensor in the transmitter coordinate system, we first convert so that we have the P&O of the transmitter in the sensor coordinate frame. The procedure then proceeds as above. The mutual inductance $L_{13}$ is computed by calculating the P&O of the transmitter in the ring coordinate system. The relationship between the ring and the sensor is known and fixed as noted above, so once the transmitter P&O is known relative to the sensor, conversion transformations are obvious. Next compute the magnetic field per unit current produced by the ring at the sensor location. Finally, the mutual inductance term is calculated for each sensor coil by taking the dot product between the coil vector and the field, using the point source property of the dipole approximation.

With all of the inductance terms available, Equation 6 is then readily calculated. Overall, the approach of measuring mutual inductances allows the system to develop robust measurements in which reliance on references such as $Z_{ref}$ or a signal ratio, or use of a common preamplifier with high precision output digitization, have eliminated numerous sources of variability while allowing effective use of small magnetic assemblies to achieve accuracy and resolution.

Moreover, by introducing a shield or virtual distorter and fixing a receiver assembly with respect to the shield, the effects of individual distortion environments are substantially eliminated, and the shield itself may be effectively modeled, eliminating the cumbersome requirement of compiling a mapping or calibration table. The model may then produce a seed calculation, allowing computationally effective fitting processes to replace the cumbersome calculations of the prior art. In other words, a distorter that is shaped to optimally shield magnetic fields from existing environmental distorters can be utilized without any regard for a specific desired field shape. The shield's effect on the field can then be modeled, or alternatively, mapped.

The invention being thus disclosed and illustrative embodiments depicted herein, further variations and modifications of the invention will occur to those skilled in the art, and all such variations and modifications are considered to be within the scope of the invention, as defined by the claims appended hereto and equivalents thereof.

APPENDIX A

Derivation of Mutual Inductance Between Two Dipole Coils

Here, we derive the mutual inductance between two magnetic dipole coils:

$$L_m = \frac{\mu_o AB}{4\pi R^3}\left(3(\hat{a}\cdot\hat{r})(\hat{r}\cdot\hat{b}) - \hat{a}\cdot\hat{b}\right) \quad (A.1)$$

where
- $\hat{a}$=unit vector in direction of dipole A
- A=magnitude of effective area of dipole A
- $\hat{b}$=unit vector in direction of dipole B
- B=magnitude of effective area of dipole B
- $\hat{r}$=unit vector in direction from center of dipole A to center of dipole B
- R=magnitude of distance from center of dipole A to center of dipole B Each dipole is replaced by a small but finite-sized single-turn square coil. Each coil is shrunk to an infinitesimal size (while increasing its number of turns to infinity) to obtain the dipole limit. In the dipole limit, the shape of the coil does not matter. The coil's properties are described by the coil's effective area, the product of the coil's geometrical area and number of turns.

The mutual inductance, $L_m$ between two closed circuits is given by Neuman's formula:

$$L_m = \frac{\mu_0}{4\pi}\oint_{circuit\,A}\oint_{circuit\,B}\frac{d\overline{s_A}\cdot d\overline{s_B}}{r_{AB}} \quad (A.2)$$

where
$r_{AB}$=distance between point on circuit A and point on circuit B
$\mu_o = 4\pi 10^{-7}$ henries/meter Here, we consider the case where each circuit is composed of four straight-line segments.

Define some quantities:
- $\overline{A}=A\hat{a}$=effective area of dipole A
- $\hat{u}$ and $\hat{v}$ are two unit vectors such that $\hat{a}=\hat{u}\times\hat{v}$
- $\overline{B}=B\hat{b}$=effective area of dipole B
- $\hat{p}$ and $\hat{q}$ are two unit vectors such that $\hat{b}=\hat{p}\times\hat{q}$
- h=a small dimensionless scalar which goes to zero in the dipole limit
- $\overline{R}=R\hat{r}$=vector from center of dipole A to center of dipole B Use the $\hat{u}$, $\hat{v}$, $\hat{a}$ cartesian coordinate system, where dipole A is at the origin and dipole B is at $\overline{R}=R\hat{r}=u\hat{u}+v\hat{v}+a\hat{a}$.

The four corners of coil A are:

$$\overline{A_1} = \frac{h}{2}\hat{u} + \frac{h}{2}\hat{v}$$

$$\overline{A_2} = \frac{h}{2}\hat{u} - \frac{h}{2}\hat{v}$$

$$\overline{A_3} = -\frac{h}{2}\hat{u} - \frac{h}{2}\hat{v}$$

$$\overline{A_4} = -\frac{h}{2}\hat{u} + \frac{h}{2}\hat{v}$$

Note that the ratio of the effective area of dipole A to the effective area of coil A is $$\frac{A}{h^3}.$$

A point on coil A is given by:

$$(\mu,v)=\mu\hat{u}+v\hat{v}$$

where $\mu$ has nothing to do with $\mu_o$.

The four corners of coil B are:

$$\overline{B_1} = \frac{h}{2}\hat{p} + \frac{h}{2}\hat{q} + \overline{R}$$

$$\overline{B_2} = \frac{h}{2}\hat{p} - \frac{h}{2}\hat{q} + \overline{R}$$

$$\overline{B_3} = -\frac{h}{2}\hat{p} - \frac{h}{2}\hat{q} + \overline{R}$$

$$\overline{B_4} = -\frac{h}{2}\hat{p} + \frac{h}{2}\hat{q} + \overline{R}$$

Note that the ratio of the effective area of dipole B to the effective area of coil B is $$\frac{B}{h^2}.$$

A point on coil B is given by:

$$(p,q)=p\hat{p}+q\hat{q}+\overline{R}$$

The distance from a point on coil A to a point on coil B is:

$$r_{AB}=|\overline{s_A}-p\hat{p}-q\hat{q}|$$

where the vector from center of coil B to the point on coil A is:

$$\overline{s_A}=\mu\hat{u}+v\hat{v}-\overline{R}$$

Expand the integral around circuit B in equation A.2 by explicitly going around circuit B from point $\overline{B_4}$ through points $\overline{B_1}$, $\overline{B_2}$, $\overline{B_3}$, and back to point $\overline{B_4}$:

$$L_m = \frac{\mu_o}{4\pi}\lim_{h\to 0}\frac{B}{h^2}\oint_A\int_{-\frac{h}{2}}^{+\frac{h}{2}}\left(\frac{\hat{p}db}{\left|\overline{s_A}-bh\hat{p}-\frac{h}{2}\hat{q}\right|} - \frac{\hat{q}db}{\left|\overline{s_A}-\frac{h}{2}\hat{p}+bh\hat{q}\right|} - \frac{\hat{p}db}{\left|\overline{s_A}+bh\hat{p}+\frac{h}{2}\hat{q}\right|} + \frac{\hat{q}db}{\left|\overline{s_A}+\frac{h}{2}\hat{p}-bh\hat{q}\right|}\right)\cdot d\overline{s_A} \quad (A.3)$$

Define g to be the inverse of the distance from a point on coil A to a point on coil B:

$$g = \frac{1}{r_{AB}} = \frac{1}{|\overline{s_A}+p\hat{p}+q\hat{q}|} \quad (A.4)$$

Calculate some directional partial derivatives along the $\hat{p}$ and $\hat{q}$ axes, remembering that $\overline{s_A}$ is independent of p and q:

$$\left[\frac{\partial g}{\partial p}\right]_{p=0}^{q=\frac{h}{2}} = \frac{\partial}{\partial p}\left[\frac{1}{|\overline{s_A} - p\hat{p} - q\hat{q}|}\right]_{p=0,q=\frac{h}{2}} = \tag{A.5}$$

$$\lim_{\epsilon \to 0}\frac{1}{2b\epsilon}\left(\frac{1}{\left|\overline{s_A} - b\epsilon\hat{p} - \frac{h}{2}\hat{q}\right|} - \frac{1}{\left|\overline{s_A} + b\epsilon\hat{p} - \frac{h}{2}\hat{q}\right|}\right)$$

$$\left[\frac{\partial g}{\partial q}\right]_{p=-bh}^{q=0} = \frac{\partial}{\partial p}\left[\frac{1}{|\overline{s_A} - p\hat{p} - q\hat{q}|}\right]_{p=-bh,q=0} = \tag{A.6}$$

$$\lim_{\epsilon \to 0}\frac{1}{\epsilon}\left(\frac{1}{\left|\overline{s_A} + bh\hat{p} - \frac{\epsilon}{2}\hat{q}\right|} - \frac{1}{\left|\overline{s_A} + bh\hat{p} + \frac{\epsilon}{2}\hat{q}\right|}\right)$$

$$\left[\frac{\partial g}{\partial p}\right]_{p=0}^{q=-bh} = \frac{\partial}{\partial p}\left[\frac{1}{|\overline{s_A} - p\hat{p} - q\hat{q}|}\right]_{p=0,q=-bh} = \tag{A.7}$$

$$\lim_{\epsilon \to 0}\frac{1}{\epsilon}\left(\frac{1}{\left|\overline{s_A} - \frac{\epsilon}{2}\overline{p} + bh\hat{q}\right|} - \frac{1}{\left|\overline{s_A} + \frac{\epsilon}{2}\overline{p} + bh\hat{q}\right|}\right)$$

$$\left[\frac{\partial g}{\partial q}\right]_{p=-\frac{h}{2}}^{q=0} = \frac{\partial}{\partial q}\left[\frac{1}{|\overline{s_A} - p\hat{p} - q\hat{q}|}\right]_{p=-\frac{h}{2},q=0} = \tag{A.8}$$

$$\lim_{\epsilon \to 0}\frac{1}{2b\epsilon}\left(\frac{1}{\left|\overline{s_A} + \frac{h}{2}\hat{p} - b\epsilon\hat{q}\right|} - \frac{1}{\left|\overline{s_A} + \frac{h}{2}\hat{p} - b\epsilon\hat{q}\right|}\right)$$

Set $\epsilon = h$, and substitute into equation A.3:

$$L_m = \tag{A.9}$$

$$\frac{\mu_o B}{4\pi}\lim_{h\to 0}\frac{1}{h}\oint_A \int_{-\frac{h}{2}}^{+\frac{h}{2}}\left(2b\hat{p}\left[\frac{\partial g}{\partial p}\right]_{p=0}^{q=\frac{h}{2}} + \hat{p}\left[\frac{\partial g}{\partial q}\right]_{p=-bh}^{q=0} - \hat{q}\left[\frac{\partial g}{\partial p}\right]_{p=0}^{q=-bh} + 2b\hat{q}\left[\frac{\partial g}{\partial q}\right]_{p=-\frac{h}{2}}^{q=0}\right)db \cdot d\overline{s_A}$$

Perform the integration over b:

$$L_m = \frac{\mu_o B}{4\pi}\lim_{h\to 0}\oint_A\left(\hat{p}\left[\frac{\partial g}{\partial q}\right]_{p=-bh}^{q=0} - \hat{q}\left[\frac{\partial g}{\partial p}\right]_{p=0}^{q=-bh}\right)\cdot d\overline{s_A} \tag{A.10}$$

Expand the integral around circuit A in equation A.10 by explicitly going around circuit A from point $\overline{A_4}$ through points $\overline{A_1}$, $\overline{A_2}$, $\overline{A_3}$, and back to point $\overline{A_4}$:

$$L_m = \frac{\mu_o B}{4\pi}\lim_{h\to 0}(I_1 + I_2 + I_3 + I_4) \tag{A.11}$$

where:

$$I_1 = \frac{A}{h^2}\int_{-\frac{h}{2}}^{\frac{h}{2}}\left(\hat{p}\left[\frac{\partial g}{\partial q}\right]_{p=q=0} - \hat{q}\left[\frac{\partial g}{\partial p}\right]_{p=q=0}\right)_{v=\frac{h}{2}}\cdot \hat{u}\,d\mu \tag{A.12}$$

$$I_2 = -\frac{A}{h^2}\int_{-\frac{h}{2}}^{\frac{h}{2}}\left(\hat{p}\left[\frac{\partial g}{\partial q}\right]_{p=q=0} - \hat{q}\left[\frac{\partial g}{\partial p}\right]_{p=q=0}\right)_{\mu=\frac{h}{2}}\cdot \hat{v}\,dv \tag{A.13}$$

-continued $$I_3 = -\frac{A}{h^2}\int_{-\frac{h}{2}}^{\frac{h}{2}}\left(\hat{p}\left[\frac{\partial g}{\partial q}\right]_{p=q=0} - \hat{q}\left[\frac{\partial g}{\partial p}\right]_{p=q=0}\right)_{v=-\frac{h}{2}}\cdot \hat{u}\,d\mu \tag{A.14}$$

$$I_4 = \frac{A}{h^2}\int_{-\frac{h}{2}}^{\frac{h}{2}}\left(\hat{p}\left[\frac{\partial g}{\partial q}\right]_{p=q=0} - \hat{q}\left[\frac{\partial g}{\partial p}\right]_{p=q=0}\right)_{\mu=-\frac{h}{2}}\cdot \hat{v}\,dv \tag{A.15}$$

Rearrange to separate the four dotproducts:

$$L_m = \frac{\mu_o AB}{4\pi}\lim_{h\to 0}(I_{pu}\hat{p}\cdot\hat{u} - I_{qu}\hat{q}\cdot\hat{u} - I_{pv}\hat{p}\cdot\hat{v} + I_{qv}\hat{q}\cdot\hat{v}) \tag{A.16}$$

where:

$$I_{pu} = \frac{1}{h^2}\int_{-\frac{h}{2}}^{\frac{h}{2}}\left(\left[\frac{\partial g}{\partial q}\right]_{p=q=0}^{v=\frac{h}{2}} - \left[\frac{\partial g}{\partial q}\right]_{p=q=0}^{v=-\frac{h}{2}}\right)d\mu \tag{A.17}$$

$$I_{qu} = \frac{1}{h^2}\int_{-\frac{h}{2}}^{\frac{h}{2}}\left(\left[\frac{\partial g}{\partial p}\right]_{p=q=0}^{v=\frac{h}{2}} - \left[\frac{\partial g}{\partial p}\right]_{p=q=0}^{v=-\frac{h}{2}}\right)d\mu \tag{A.18}$$

$$I_{pv} = \frac{1}{h^2}\int_{-\frac{h}{2}}^{\frac{h}{2}}\left(\left[\frac{\partial g}{\partial q}\right]_{p=q=0}^{\mu=\frac{h}{2}} - \left[\frac{\partial g}{\partial q}\right]_{p=q=0}^{\mu=-\frac{h}{2}}\right)dv \tag{A.19}$$

$$I_{qv} = \frac{1}{h^2}\int_{-\frac{h}{2}}^{\frac{h}{2}}\left(\left[\frac{\partial g}{\partial p}\right]_{p=q=0}^{\mu=\frac{h}{2}} - \left[\frac{\partial g}{\partial p}\right]_{p=q=0}^{\mu=-\frac{h}{2}}\right)dv \tag{A.20}$$

Apply the definition of a partial derivative and the fact that h is small to equations A.17, A.18, A.19, and A.20:

$$I_{pu} = \frac{1}{h}\int_{-\frac{h}{2}}^{\frac{h}{2}}\left[\frac{\partial^2 g}{\partial v \partial q}\right]_{p=q=0}^{\mu=v=0}d\mu = \left[\frac{\partial^2 g}{\partial v \partial q}\right]_{p=q=0}^{\mu=v=0} \tag{A.21}$$

$$I_{qu} = \frac{1}{h}\int_{-\frac{h}{2}}^{\frac{h}{2}}\left[\frac{\partial^2 g}{\partial v \partial p}\right]_{p=q=0}^{\mu=v=0}d\mu = \left[\frac{\partial^2 g}{\partial v \partial p}\right]_{p=q=0}^{\mu=v=0} \tag{A.22}$$

$$I_{pv} = \frac{1}{h}\int_{-\frac{h}{2}}^{\frac{h}{2}}\left[\frac{\partial^2 g}{\partial \mu \partial q}\right]_{p=q=0}^{\mu=v=0}dv = \left[\frac{\partial^2 g}{\partial \mu \partial q}\right]_{p=q=0}^{\mu=v=0} \tag{A.23}$$

$$I_{qv} = \frac{1}{h}\int_{-\frac{h}{2}}^{\frac{h}{2}}\left[\frac{\partial^2 g}{\partial \mu \partial p}\right]_{p=q=0}^{\mu=v=0}dv = \left[\frac{\partial^2 g}{\partial \mu \partial p}\right]_{p=q=0}^{\mu=v=0} \tag{A.24}$$

Recall that g is:

$$g = \frac{1}{T_{AB}} = \frac{1}{|\mu\hat{u} + v\hat{v} - \overline{R} - p\hat{p} - q\hat{q}|} \tag{A.25}$$

$$= \frac{1}{|(\mu - u)\hat{u} + (v - v)\hat{v} - a\hat{a} - p\hat{p} - q\hat{q}|}$$

Then:

$$I_{pu} = \left[\frac{\partial^2 g}{\partial v \partial q}\right]_{p=q=0}^{\mu=v=0} = -\left[\frac{\partial^2 g}{\partial v \partial q}\right]_{p=q=0}^{\mu=v=0} \tag{A.26}$$

$$I_{qu} = \left[\frac{\partial^2 g}{\partial v \partial p}\right]_{p=q=0}^{\mu=v=0} = -\left[\frac{\partial^2 g}{\partial v \partial p}\right]_{p=q=0}^{\mu=v=0} \tag{A.27}$$

-continued $$I_{pv} = \left[\frac{\partial^2 g}{\partial \mu \partial q}\right]_{p=q=0}^{\mu=v=0} = -\left[\frac{\partial^2 g}{\partial u \partial q}\right]_{p=q=0}^{\mu=v=0} \quad (A.28)$$

$$I_{qv} = \left[\frac{\partial^2 g}{\partial \mu \partial p}\right]_{p=q=0}^{\mu=v=0} = -\left[\frac{\partial^2 g}{\partial u \partial p}\right]_{p=q=0}^{\mu=v=0} \quad (A.29)$$

Substitute into equation A.16:

$$L_m = \frac{\mu_o AB}{4\pi} \quad (A.30)$$

$$\left(-\frac{\partial^2 g}{\partial v \partial q}\hat{p}\cdot\hat{u} + \frac{\partial^2 g}{\partial v \partial p}\hat{q}\cdot\hat{u} + \frac{\partial^2 g}{\partial u \partial q}\hat{p}\cdot\hat{v} - \frac{\partial^2 g}{\partial u \partial p}\hat{q}\cdot\hat{v}\right)$$

Calculate g in equation A.30 and its partial derivatives in the û, v̂, â cartesian coordinate system, where dipole A is at the origin and dipole B is at $\overline{R}=R\hat{r}+v\hat{v}+a\hat{a}$:

$$g = \frac{1}{R} = \frac{1}{\sqrt{u^2+v^2+a^2}}$$

$$\frac{\partial g}{\partial p} = \hat{p}\cdot\hat{u}\frac{\partial g}{\partial u} + \hat{p}\cdot\hat{v}\frac{\partial g}{\partial v} + \hat{p}\cdot\hat{a}\frac{\partial g}{\partial a} = -g^3(\hat{p}\cdot\hat{u}u + \hat{p}\cdot\hat{v}v + \hat{p}\cdot\hat{a}a)$$

$$\frac{\partial^2 g}{\partial u \partial p} = 3g^5(\hat{p}\cdot\hat{u}u + \hat{p}\cdot\hat{v}v + \hat{p}\cdot\hat{a}a)u - g^3\hat{p}\cdot\hat{u}$$

$$\frac{\partial^2 g}{\partial v \partial p} = 3g^5(\hat{p}\cdot\hat{u}u + \hat{p}\cdot\hat{v}v + \hat{p}\cdot\hat{a}a)v - g^3\hat{p}\cdot\hat{v}$$

$$\frac{\partial g}{\partial q} = \hat{q}\cdot\hat{u}\frac{\partial g}{\partial u} + \hat{q}\cdot\hat{v}\frac{\partial g}{\partial v} + \hat{q}\cdot\hat{a}\frac{\partial g}{\partial a} = -g^3(\hat{q}\cdot\hat{u}u + \hat{q}\cdot\hat{v}v + \hat{q}\cdot\hat{a}a)$$

$$\frac{\partial^2 g}{\partial u \partial q} = 3g^5(\hat{q}\cdot\hat{u}u + \hat{q}\cdot\hat{v}v + \hat{q}\cdot\hat{a}a)u - g^3\hat{q}\cdot\hat{u}$$

$$\frac{\partial^2 g}{\partial v \partial q} = 3g^5(\hat{q}\cdot\hat{u}u + \hat{q}\cdot\hat{v}v + \hat{q}\cdot\hat{a}a)v - g^3\hat{q}\cdot\hat{v}$$

Substitute into equation A.30:

$$L_m = \frac{\mu_o AB}{4\pi R^3}\left(\frac{-3}{R^2}F - T\right) \quad (A.31)$$

where $T=2((\hat{p}\cdot\hat{v})(\hat{q}\cdot\hat{u})-(\hat{p}\cdot\hat{u})(\hat{q}\cdot\hat{v}))=-2(\hat{a}\cdot\hat{b})$ and $F=(\hat{q}\cdot\hat{u}u+\hat{q}\cdot\hat{v}v+\hat{q}\cdot\hat{a}a)\hat{p}\cdot\hat{u}v-(\hat{p}\cdot\hat{u}u+\hat{p}\cdot\hat{v}v+\hat{p}\cdot\hat{a}a)\hat{q}\cdot\hat{u}v-(\hat{q}\cdot\hat{u}u+\hat{q}\cdot\hat{v}v+\hat{q}\cdot\hat{a}a)\hat{p}\cdot\hat{v}u+(\hat{p}\cdot\hat{u}u+\hat{p}\cdot\hat{v}v+\hat{p}\cdot\hat{a}a)\hat{q}\cdot\hat{u}u$ Expand F:

$F=(\hat{q}\cdot\hat{u})(\hat{p}\cdot\hat{u})vu+(\hat{q}\cdot\hat{v})(\hat{p}\cdot\hat{u})v^2+(\hat{q}\cdot\hat{a})(\hat{p}\cdot\hat{u})va-(\hat{p}\cdot\hat{u})(\hat{q}\cdot\hat{u})vu-(\hat{p}\cdot\hat{v})(\hat{q}\cdot\hat{u})v^2-\hat{p}\cdot\hat{a}(\hat{q}\cdot\hat{u})va-(\hat{q}\cdot\hat{u})(\hat{p}\cdot\hat{v})u^2-(\hat{q}\cdot\hat{v})(\hat{p}\cdot\hat{v})uv-(\hat{q}\cdot\hat{a})(\hat{p}\cdot\hat{v})ua+(\hat{p}\cdot\hat{u})(\hat{q}\cdot\hat{v})u^2+(\hat{p}\cdot\hat{v})(\hat{q}\cdot\hat{v})uv+(\hat{p}\cdot\hat{a})(\hat{q}\cdot\hat{v})ua$ Rearrange terms:

$F=+(\hat{q}\cdot\hat{a})(\hat{p}\cdot\hat{a})va-(\hat{p}\cdot\hat{a})(\hat{q}\cdot\hat{u})va+(\hat{p}\cdot\hat{a})(\hat{q}\cdot\hat{v})ua-(\hat{q}\cdot\hat{a})(\hat{p}\cdot\hat{v})ua-(\hat{q}\cdot\hat{u})(\hat{p}\cdot\hat{v})u^2+(\hat{p}\cdot\hat{u})(\hat{q}\cdot\hat{v})u^2+(\hat{q}\cdot\hat{v})(\hat{p}\cdot\hat{u})v^2-(\hat{p}\cdot\hat{v})(\hat{q}\cdot\hat{u})v^2+(\hat{q}\cdot\hat{u})(\hat{p}\cdot\hat{u})vu-(\hat{p}\cdot\hat{u})(\hat{q}\cdot\hat{u})vu-(\hat{p}\cdot\hat{v})(\hat{q}\cdot\hat{v})uv+(\hat{p}\cdot\hat{v})(\hat{q}\cdot\hat{v})uv$ Eliminate cancelling terms at end:

$F=+(\hat{q}\cdot\hat{a})(\hat{p}\cdot\hat{a})va-(\hat{p}\cdot\hat{a})(\hat{q}\cdot\hat{u})va+(\hat{p}\cdot\hat{a})(\hat{q}\cdot\hat{v})ua-(\hat{q}\cdot\hat{a})(\hat{p}\cdot\hat{v})ua-(\hat{q}\cdot\hat{u})(\hat{p}\cdot\hat{v})u^2+(\hat{p}\cdot\hat{u})(\hat{q}\cdot\hat{v})u^2+(\hat{q}\cdot\hat{v})(\hat{p}\cdot\hat{u})v^2-(\hat{p}\cdot\hat{v})(\hat{q}\cdot\hat{u})v^2$ Insert new cancelling terms at end:

$F=+(\hat{q}\cdot\hat{a})(\hat{p}\cdot\hat{a})va-(\hat{p}\cdot\hat{a})(\hat{q}\cdot\hat{u})va+(\hat{p}\cdot\hat{a})(\hat{q}\cdot\hat{v})ua-(\hat{q}\cdot\hat{a})(\hat{p}\cdot\hat{v})ua-(\hat{q}\cdot\hat{u})(\hat{p}\cdot\hat{v})u^2+(\hat{p}\cdot\hat{u})(\hat{q}\cdot\hat{v})u^2+(\hat{q}\cdot\hat{v})(\hat{p}\cdot\hat{u})v^2-(\hat{p}\cdot\hat{v})(\hat{q}\cdot\hat{u})v^2-(\hat{p}\cdot\hat{u})(\hat{q}\cdot\hat{v})a^2+(\hat{p}\cdot\hat{v})(\hat{q}\cdot\hat{u})a^2+(\hat{p}\cdot\hat{u})(\hat{q}\cdot\hat{v})a^2-(\hat{p}\cdot\hat{v})(\hat{q}\cdot\hat{u})a^2$ Since $\hat{a}=\hat{u}\times\hat{v}$ and $\hat{b}=\hat{p}\times\hat{q}$, we have:

$-\hat{a}\cdot\hat{b}=(\hat{p}\cdot\hat{v})(\hat{q}\cdot\hat{u})-(\hat{p}\cdot\hat{u})(\hat{q}\cdot\hat{v})$ Apply this equality in the $u^2$ and $v^2$ terms in F:

$F=+(\hat{p}\cdot\hat{u})(\hat{q}\cdot\hat{a})va-(\hat{p}\cdot\hat{a})(\hat{q}\cdot\hat{u})va-(\hat{p}\cdot\hat{v})(\hat{q}\cdot\hat{a})ua+(\hat{p}\cdot\hat{a})(\hat{q}\cdot\hat{v})ua+(\hat{a}\cdot\hat{b})u^2+(\hat{a}\cdot\hat{b})v^2-(\hat{p}\cdot\hat{u})(\hat{q}\cdot\hat{v})a^2+(\hat{p}\cdot\hat{v})(\hat{q}\cdot\hat{u})a^2$ Rearrange terms:

$F=-(\hat{p}\cdot\hat{a})(\hat{q}\cdot\hat{u})va+(\hat{p}\cdot\hat{u})(\hat{q}\cdot\hat{a})va-(\hat{p}\cdot\hat{u})(\hat{q}\cdot\hat{v})a^2+(\hat{p}\cdot\hat{v})(\hat{q}\cdot\hat{u})a^2-(\hat{p}\cdot\hat{v})(\hat{q}\cdot\hat{a})ua+(\hat{p}\cdot\hat{a})(\hat{q}\cdot\hat{v})ua+(\hat{a}\cdot\hat{b})u^2+(\hat{a}\cdot\hat{b})v^2$ Recall that $R^2=u^2+v^2+a^2$, and substitute for last three terms:

$F=-(\hat{p}\cdot\hat{a})(\hat{q}\cdot\hat{u})va+(\hat{p}\cdot\hat{u})(\hat{q}\cdot\hat{a})va-(\hat{p}\cdot\hat{u})(\hat{q}\cdot\hat{v})a^2+(\hat{p}\cdot\hat{v})(\hat{q}\cdot\hat{u})a^2-(\hat{p}\cdot\hat{v})(\hat{q}\cdot\hat{a})ua+(\hat{p}\cdot\hat{a})(\hat{q}\cdot\hat{v})ua+(\hat{a}\cdot\hat{b})R^2$ Since $\hat{a}=\hat{u}\times\hat{v}$ and $\hat{b}=\hat{p}\times\hat{q}$, we have:

$$\hat{a}\cdot\hat{r} = \frac{a}{R}$$

and $$(\hat{a}\cdot\hat{r})(\hat{b}\cdot\hat{r}) = \frac{(\hat{p}\cdot\hat{a})(\hat{q}\cdot\hat{u})va - (\hat{p}\cdot\hat{u})(\hat{q}\cdot\hat{a})va + (\hat{p}\cdot\hat{u})(\hat{q}\cdot\hat{v})a^2 - (\hat{p}\cdot\hat{v})(\hat{q}\cdot\hat{u})a^2 + (\hat{p}\cdot\hat{v})(\hat{q}\cdot\hat{a})ua - (\hat{p}\cdot\hat{a})(\hat{q}\cdot\hat{u})va}{R^2}$$

Then:

$F = -(\hat{a}\cdot\hat{r})(\hat{b}\cdot\hat{r})R^2 + (\hat{a}\cdot\hat{b})R^2$

Substitute F and T into equation A.31:

$$L_m = \frac{\mu_o AB}{4\pi R^3}(3(\hat{a}\cdot\hat{r})(\hat{b}\cdot\hat{r}) - 3(\hat{a}\cdot\hat{b}) + 2(\hat{a}\cdot\hat{b})) \quad (A.32)$$

Simplify to get result A.1:

$$L_m = \frac{\mu_o AB}{4\pi R^3}(3(\hat{a}\cdot\hat{r})(\hat{r}\cdot\hat{b}) - (\hat{a}\cdot\hat{b})) \quad (A.33)$$

We can write equation A.33 rising a dyadic operator:

$$L_m = \frac{\mu_o AB}{4\pi R^3}\hat{a}\cdot D\cdot\hat{b} \quad (A.34)$$

If the vectors â, b̂ and r̂ are three-element row vectors, then the dyadic operator D can be written as a 3×3 matrix, and the dot products are matrix multiplies:

$$L_m = \frac{\mu_o AB}{4\pi R^3}\hat{a}D\hat{b}^t \quad (A.35)$$

where D is given by (I is the 3×3 identity matrix):

$$D = 3\hat{r}\hat{r} - I \qquad (A.36)$$

APPENDIX B

Derivation of Orthogonal-dipole Seed Calculation

Given the dipole model of mutual inductances $L_{tr}$ is functions of position $\overline{R}$ and orientation O, we calculate $\overline{R}$ and O in terms of $L_{tr}$.

To use the result as a P&O algorithm seed, we calculate estimated values of $\overline{R}$ and O from measured values of $L_{tr}$.

We make the dipole approximation, that the dimensions of each coil are small compared to the distance between coils.

We have three equal-effective area colocated orthogonal dipole transmitter coils and three equal-effective-area colocated orthogonal dipole receiver coils. We derived the mutual inductance of two dipoles in Appendix A, so we start with a 3×3 mutual-inductance matrix:

$$L_{tr} = \frac{\mu_o A_t A_r}{4\pi R^3}\left(3(\hat{t}\cdot\hat{R})(\hat{R}\cdot\hat{r}) - (\hat{t}\cdot\hat{r})\right) \qquad (B.1)$$

where
t=transmitter coil 0,1, or 2
r=receiver coil 0,1, or 2
$\mu_o = 4\pi 10^{-7}$ henries/meter
R=magnitude of distance from dipole t to dipole T
$\hat{R}$=unit vector pointing from dipole t to dipole r
$A_t$=magnitude of transmitter dipole effective area independent of t
$A_r$=magnitude of receiver dipole effective area independent of r
$\hat{t}$=unit vector pointing in direction of dipole t effective area
$\hat{r}$=unit vector pointing in direction of dipole r effective area The transmitter effective area vector $\overline{A_t}$ is:
$\overline{A_t} = A_t \hat{t}$
The receiver effective area vector $\overline{A_r}$ is:
$\overline{A_r} = A_r \hat{r}$
Define the cartesian coordinate system:
$\hat{X}=(1,0,0)$ unit vector in +X direction
$\hat{Y}=(0,1,0)$ unit vector in +Y direction
$\hat{Z}=(0,0,1)$ unit vector in +Z direction
The receiver position vector $\overline{R}$ is independent of t and r, and has cartesian coordinates $R_x$, $R_y$, and $R_z$:

$\overline{R} = R\hat{R} = R_x\hat{X} + R_y\hat{Y} + R_z\hat{Z}$

We have three transmitter dipoles, 0, 1 and 2, which are centered on the origin, orthogonal to each other, all the same effective area Ar, and pointing along the X, Y, and Z axes respectively:
When t=0, $\hat{t}=\hat{X}$.
When t=1, $\hat{t}=\hat{Y}$.
When t=2, $\hat{t}=\hat{Z}$.
Define a rotated cartesian coordinate system for the receiver dipoles, to represent the receiver orientation:
$\hat{X}_r$=unit vector in rotated +X direction
$\hat{Y}_r$=unit vector in rotated +Y direction
$\hat{Z}_r$=unit vector in rotated +Z direction
We represent the receiver orientation as a normalized rotation quaternion O. Then we calculate $\hat{X}_r$, $\hat{Y}_r$ and $\hat{Z}_r$ by representating each vector as a pure-imaginary quaternion (O' is the quaternion complement of O):

$(0, \hat{X}_r) = O(0,1,0,0)O'$
$(0, \hat{Y}_r) = O(0,0,1,0)O'$
$(0, \hat{Z}_r) = O(0,0,0,1)O'$ We have three receiver dipoles, 0, 1 and 2, which are centered on the point R, orthogonal to each other, all the same effective area Ar, and pointing along the $X_r$, $Y_r$ and $Z_r$ axes respectively:
When r=0, $\hat{r}=\hat{X}_r$.
When r=1, $\hat{r}=\hat{Y}_r$.
When r=2, $\hat{r}=\hat{Z}_r$.
Define K, which is independent of $\overline{R}$, O, and Ltr:

$$K = \frac{\mu_o A_t A_r}{4\pi}$$

Now B.1 becomes:

$$L_{tr} = \frac{K}{R^3}\left(3(\hat{t}\cdot\hat{R})(\hat{r}\cdot\hat{R}) - (\hat{t}\cdot\hat{r})\right) \qquad (B.2)$$

$L_t^2$ is independent of O. We use this fact to solve for $\overline{R}$.
From B.2, the square of the mutual inductance of one transmitter dipole and one receiver dipole is:

$$L_{tr}^2 = \frac{K^2}{R^6}\left(9(\hat{t}\cdot\hat{R})^2(\hat{r}\cdot\hat{R})^2 - 6((\hat{t}\cdot\hat{R})(\hat{r}\cdot\hat{R})(\hat{t}\cdot\hat{r})) + (\hat{t}\cdot\hat{r})^2\right) \qquad (B.3)$$

Then, the sum of the squares of the mutual inductances of one transmitter dipole and the three receiver dipoles, is:

$$L_t^2 = \frac{K^2}{R^6}\left(3(\hat{t}\cdot\hat{R})^2 + 1\right) \qquad (B.4)$$

For transmitter coil 0:

$$L_0^2 = \frac{K^2}{R^6}\left(3\left(\frac{Rx}{R}\right)^2 + 1\right) \qquad (B.5)$$

For transmitter coil 1:

$$L_1^2 = \frac{K^2}{R^6}\left(3\left(\frac{Ry}{R}\right)^2 + 1\right) \qquad (B.6)$$

For transmitter coil 2:

$$L_2^2 = \frac{K^2}{R^6}\left(3\left(\frac{Rz}{R}\right)^2 + 1\right) \qquad (B.7)$$

The sum of the squares of all nine mutual inductances is then:

$$L_{tot}^2 = 6\frac{K^2}{R^6} \quad (B.8)$$

Solve B.8 for R:

$$R = \left(\frac{6K^2}{L_{tot}^2}\right)^{\frac{1}{6}} \quad (B.9)$$

Solve B.5, B.6, and B.7 for $Rx^2$, $Ry^2$ and $Rz^2$ respectively, and use B.8 and B.9 to eliminate R:

$$R_x^2 = \left(2\frac{L_0^2}{L_{tot}^2} - \frac{1}{3}\right)\left(\frac{6K^2}{L_{tot}^2}\right)^{\frac{1}{3}} \quad (B.10)$$

$$R_y^2 = \left(2\frac{L_1^2}{L_{tot}^2} - \frac{1}{3}\right)\left(\frac{6K^2}{L_{tot}^2}\right)^{\frac{1}{3}} \quad (B.11)$$

$$R_z^2 = \left(2\frac{L_2^2}{L_{tot}^2} - \frac{1}{3}\right)\left(\frac{6K^2}{L_{tot}^2}\right)^{\frac{1}{3}} \quad (B.12)$$

Now we take the square roots of these three quantities:

$$R_x = (+ \text{ or } -)\sqrt{\left(2\frac{L_0^2}{L_{tot}^2} - \frac{1}{3}\right)\left(\frac{6K^2}{L_{tot}^2}\right)^{\frac{1}{3}}} \quad (B.13)$$

$$R_y = (+ \text{ or } -)\sqrt{\left(2\frac{L_0^2}{L_{tot}^2} - \frac{1}{3}\right)\left(\frac{6K^2}{L_{tot}^2}\right)^{\frac{1}{3}}} \quad (B.14)$$

$$R_z = (+ \text{ or } -)\sqrt{\left(2\frac{L_0^2}{L_{tot}^2} - \frac{1}{3}\right)\left(\frac{6K^2}{L_{tot}^2}\right)^{\frac{1}{3}}} \quad (B.15)$$

The signs of Rx, Ry, and Rz are determined from the signs of products of the mutual inductances.

Due to the symmetries of the fields, positions $\overline{+R}$ and $\overline{-R}$, for the same orientation O, give the same mutual inductances, and cannot be distinguished by calculation. In the literature, this is called the hemisphere ambiguity.

To resolve this ambiguity, we choose to use the +X hemisphere, where $R_x$ is always positive.

Form sums of products of mutual inductances $L_{tr}$:

$$S_{01} = L_{00}L_{10} + L_{01}L_{11} + L_{02}L_{12} \quad (B.16)$$

$$S_{20} = L_{20}L_{00} + L_{21}L_{01} + L_{22}L_{02} \quad (B.17)$$

Recall that the signum or sign function is defined to be:

$sgn(x) = +1f$ or $\{x \geq 0\}$, $-1f$ or $\{x<0\}$

Then the signs of Rx, Ry, and Rz are given by:

$sgn(R_x) = +1$
$sgn(R_y) = sgn(S_{01})$
$sgn(R_z) = sgn(S_{20})$

Then the position $\overline{R}$ cartesian components are calculated in terms of the mutual inductances $L_{tr}$ by:

$$L_0^2 = L_{00}L_{00} + L_{01}L_{01} + L_{02}L_{02} \quad (B.18)$$

$$L_1^2 = L_{10}L_{10} + L_{11}L_{11} + L_{12}L_{12} \quad (B.19)$$

$$L_2^2 = L_{20}L_{20} + L_{21}L_{21} + L_{22}L_{22} \quad (B.20)$$

$$L_{tot}^2 = L_0^2 + L_1^2 + L_2^2 \quad (B.21)$$

$$R_x = +\sqrt{\left(2\frac{L_0^2}{L_{tot}^2} - \frac{1}{3}\right)\left(\frac{6K^2}{L_{tot}^2}\right)^{\frac{1}{3}}} \quad (B.22)$$

$$R_y = sgn(L_{00}L_{10} + L_{01}L_{11} + L_{02}L_{12})\sqrt{\left(2\frac{L_0^2}{L_{tot}^2} - \frac{1}{3}\right)\left(\frac{6K^2}{L_{tot}^2}\right)^{\frac{1}{3}}} \quad (B.23)$$

$$R_z = sgn(L_{20}L_{00} + L_{21}L_{01} + L_{22}L_{02})\sqrt{\left(2\frac{L_0^2}{L_{tot}^2} - \frac{1}{3}\right)\left(\frac{6K^2}{L_{tot}^2}\right)^{\frac{1}{3}}} \quad (B.24)$$

As $R_x$, $R_y$, and/or $R_z$ approach zero, B.16 and/or B.17 become numerically unstable due to small mutual inductances, and B.22, B.23, and B.24 become numerically unstable due to the square roots: Errors in the mutual inductances can cause large errors, wrong signs, or even cause a close-to-zero result to become imaginary.

Since the transmitters are colocated dipoles, and colocated dipole moments combine the same way vectors do, synthetic mutual-inductance matrices can be calculated for transmitter dipole triads with other orientations than along the X, Y, and Z axes. This solves the numerical instability of the above solution.

If the calculated position is close to the X, Y, or Z axis (and hence is numerically unstable), we can: mathematically rotate the coordinate system to move the position far from the axes, calculate the position in the rotated coordinate system (this calculation is numerically stable), then derotate the result to the original coordinate system.

In detail, the rotate, calculate, derotate algorithm is as follows:

Calculate unrotated position $\overline{R^u} = (R_x^u, R_y^u, R_z^u)$ by substituting the measured mutual inductance $L_{tr}$ in B.22, B.23, and B.24:

$$R_x^u = +\sqrt{\left(2\frac{L_0^2}{L_{tot}^2} - \frac{1}{3}\right)\left(\frac{6K^2}{L_{tot}^2}\right)^{\frac{1}{3}}} \quad (B.25)$$

$$R_y^u = sgn(L_{00}L_{10} + L_{01}L_{11} + L_{02}L_{12})\sqrt{\left(2\frac{L_0^2}{L_{tot}^2} - \frac{1}{3}\right)\left(\frac{6K^2}{L_{tot}^2}\right)^{\frac{1}{3}}} \quad (B.26)$$

$$R_z^u = sgn(L_{20}L_{00} + L_{21}L_{01} + L_{22}L_{02})\sqrt{\left(2\frac{L_0^2}{L_{tot}^2} - \frac{1}{3}\right)\left(\frac{6K^2}{L_{tot}^2}\right)^{\frac{1}{3}}} \quad (B.27)$$

If any of $R_x^u$, $R_y^u$, or $R_z^u$ come out imaginary, make that value or those values zero.

Note that the sign for a small-value $R_x^u$, $R_y^u$, or $R_z^u$ may be wrong, but this causes only a small position error, which error will be removed in following steps.

Calculate a unit vector $\hat{R}^u$ in the direction of $\overline{R^u}$:

$$\hat{R}^u = \frac{\overline{R^u}}{\sqrt{((R_x^u)^2 + (R_y^u)^2 + (R_z^u)^2)}} \quad (B.28)$$

We next calculate a unit vector $\hat{S}^u$ in the $(\text{sgn}(R_x^u), \text{sgn}(R_y^u), \text{sgn}(R_z^u))$ direction:

$$\hat{S}^u = \left(\frac{\text{sgn}(R_x^u)}{\sqrt{3}}, \frac{\text{sgn}(R_y^u)}{\sqrt{3}}, \frac{\text{sgn}(R_z^u)}{\sqrt{3}}\right) \quad (B.29)$$

Note that $S^u$ is far from the X, Y, and Z axes, and is always in the +X hemisphere.

Note that our choice of $\hat{S}^u$ means that the dot product $\hat{R}^u \cdot \hat{S}^u$ can never be negative Note that $\hat{R}^u \cdot \hat{S}^u$ analytically can never be greater than unity. Numerical errors can result in a value slightly greater than unity, but such errors do no harm here.

If $\hat{R}^u \cdot \hat{S}^u$ is greater than or equal to some threshold (we use 0.9 to 0.95), then the position estimate is numerically stable enough to be accurate, so the position is given by:

$$\overline{R} = \overline{R^u} \quad (B.30)$$

and we skip equations B.31 through B.45 below.

If the dot product is less than the threshold, then the position estimate is numerically unreliable, and we must improve the numerical stability. We do this by recalculating the position in a rotated coordinate system, and then derotating the position back to the original coordinate system.

We choose to rotate $\hat{R}^u$ into $\hat{S}^u$. Note that the rotated position vector will be far from the X, Y, and Z axes, even if the recalculation changes the position a little.

We could use any of various vector-rotation formalisms. We choose to use normalized rotation quaternions for their numerical stability and lack of singularities.

The angle between $\hat{R}^u$ and $\hat{S}^u$ is:

$$\theta = \arccos(\hat{R}^u \cdot \hat{S}^u)$$

The normalized rotation (quaternion to rotate $\hat{R}^u$ into $\hat{S}^u$ is:

$$u = \left(\cos\left(\frac{\theta}{2}\right), \frac{\hat{R}^u \times \hat{S}^u}{\cos\left(\frac{\theta}{2}\right)}\right) \quad (B.31)$$

and $$(0, \hat{S}^u) = u(0, \hat{R}^u)u' \quad (B.32)$$

Equation B.31 is numerically unstable when $\hat{R}^u$ and $\hat{S}^u$ point in close to opposite directions, i.e. when $$\left(\frac{\theta}{2}\right)$$

approaches ninety degrees. This will never happen here, because $\hat{R}^u \cdot \hat{S}^u$ is never negative.

We treat the 3×3 matrix of mutual inductances, $L_{tr}$, in B.2 as a trio of column (transposed row) vectors, one for each receiver coil; where the superscript t indicates the transpose operation:

$$L_{tr} = (L_0^t, L_1^t, L_2^t) \quad (B.33)$$

To rotate the transmitter coordinates, we apply the rotation U to each of the three row vectors in B.33:

$$(0, L_0^r) = U(0, L_0)U' \quad (B.34)$$

$$(0, L_1^r) = U(0, L_1)U' \quad (B.35)$$

$$(0, L_2^r) = U(0, L_2)U' \quad (B.36)$$

The rotated mutual-inductance matrix is:

$$L_{tr}^r = (L_0^{rt}, L_1^{rt}, L_2^{rt}) \quad (B.37)$$

Calculate rotated position $\overline{R^r} = (R_x^r, R_y^r, R_z^r)$ by substituting the rotated mutual inductances $L_{tr}^r$ in B.18 through B.24:

$$L_0^{r2} = L_{00}^r L_{00}^r + L_{01}^r L_{01}^r + L_{02}^r L_{02}^r \quad (B.38)$$

$$L_1^{r2} = L_{10}^r L_{10}^r + L_{11}^r L_{11}^r + L_{12}^r L_{12}^r \quad (B.39)$$

$$L_2^{r2} = L_{20}^r L_{20}^r + L_{21}^r L_{21}^r + L_{22}^r L_{22}^r \quad (B.40)$$

$$L_{tot}^2 = L_0^2 + L_1^2 + L_2^2 \quad (B.41)$$

$$R_x^r = +\sqrt{\left(2\frac{L_0^{r2}}{L_{tot}^{r2}} - \frac{1}{3}\right)\left(\frac{6K^2}{L_{tot}^{r2}}\right)^{\frac{1}{3}}} \quad (B.42)$$

$$R_y^r = \text{sgn}(L_{00}L_{10} + L_{01}L_{11} + L_{02}L_{12})\sqrt{\left(2\frac{L_0^2}{L_{tot}^2} - \frac{1}{3}\right)\left(\frac{6K^2}{L_{tot}^2}\right)^{\frac{1}{3}}} \quad (B.43)$$

$$R_z^r = \text{sgn}(L_{20}L_{00} + L_{21}L_{01} + L_{22}L_{02})\sqrt{\left(2\frac{L_0^2}{L_{tot}^2} - \frac{1}{3}\right)\left(\frac{6K^2}{L_{tot}^2}\right)^{\frac{1}{3}}} \quad (B.44)$$

None of $R_x^r$, $R_y^r$, or $R_z^r$ will be small, imaginary, or otherwise numerically unstable, as the rotated position is far from the axes.

Derotate the position:

$$(0, \overline{R}) = U'(0, \overline{R^r})U \quad (B.45)$$

We now have an accurate position estimate $\overline{R}$ from B.30 or B.45.

Note that we imposed the +X hemisphere restriction to force $R_x$ to be positive, but numerical effects may generate $R_x$ which is slightly negative. If $R_x$ is negative, it will be only by a value within the errors due to errors in $L_{tr}$. Physically this happens only when the physical X position is zero, putting the position on the hemisphere boundary.

We now determine an estimate for orientation. Recall that the receiver coil axes are defined by:
When r=0, $\hat{r} = \hat{X}_r$.
When r=1, $\hat{r} = \hat{Y}_r$.
When r=2, $\hat{r} = \hat{Z}_r$.

At zero orientation, the three receiver coil axes are aligned with the coordinate system axes:
When r=0, $\hat{r}^0 = \hat{X}$.
When r=1, $\hat{r}^0 = \hat{Y}$.

When r=2, $\hat{r}^0 = \hat{Z}$.

We represented the orientation as a normalized rotation quaternion O:

$$(0, \hat{X}_r) = O(0,\hat{X})O' \quad (B.46)$$

$$(0, \hat{Y}_r) = O(0,\hat{Y})O' \quad (B.47)$$

$$(0, \hat{Z}_r) = O(0,\hat{Z})O' \quad (B.48)$$

We can also represent the orientation as an orthonormal rotation matrix O, remembering that the vectors are row vectors:

$$\hat{X}_r = \hat{X}O \quad (B.49)$$

$$\hat{Y}_r = \hat{Y}O \quad (B.50)$$

$$\hat{Z}_r = \hat{Z}O \quad (B.51)$$

Equations B.49, B.50, and B.51 can be combined into one matrix equation, where the superscript t indicates the transpose of a vector or matrix:

$$(\hat{X}_r^t, \hat{Y}_r^t, \hat{Z}_r^t) = O^t(\hat{X}^t, \hat{Y}^t, \hat{Z}^t) \quad (B.52)$$

For most, orientation calculations, the rotation-matrix representation is undesireable: Rotation matrices can easily become non-orthonormal, as nine numbers in the matrix encode three degrees of freedom.

However, rotation matrices have one advantage over rotation quaternions: Equation B.52 is easily solved for the rotation matrix, where the superscript −1 indicates the inverse of a matrix:

$$O^t = (\hat{X}_r^t, \hat{Y}_r^t, \hat{Z}_r^t)(\hat{X}^t, \hat{Y}^t, \hat{Z}^t)^{-1} \quad (B.53)$$

Substituting the zero-orientation receiver unit vectors in B.2 gives $L_{tr}^0$, the mutual-inductance matrix at position $\overline{R}$ for zero orientation:

$$L_{tr}^0 = \frac{K}{R^3}\left(3(\hat{t}\cdot\hat{R})(\hat{r}^0\cdot\hat{R}) - (\hat{t}\cdot\hat{r}^0)\right) \quad (B.54)$$

In B.2 and B.54, the three mutual inductances for each receiver coil form a column vector, analogous to the column vectors in B.52. The measured mutual inductances, $L_{tr}$, thus differ from $L_{tr}^0$ by the the receiver rotation:

$$L_{tr} = O^t L_{tr}^0 \quad (B.55)$$

Solve B.55 for O:

$$O^t = L_{tr} L_{tr}^{0-1} \quad (B.56)$$

Ideally, O is an orthonormal rotation matrix describing the receiver rotation. Measurement errors and field nonidealities can easily make O deviate from orthonormality.

If matrix O is not orthonormal, we cannot convert O exactly to a rotation quaternion O. The best we can do, is to convert to a best-fit quaternion in the least-squares sense, as described by an article entitled "Closed-form solution of absolute orientation using unit quaternions" by Berthold K. P. Horn, published in "Journal of the Optical Society of America", volume 4, April, 1987, pages 629ff, herein incorporated by reference.

APPENDIX C

Mutual Inductance of Circuits of Straight-line Segments

The mutual inductance, Lm, between two closed circuits is given by Neuman's formula:

$$L_m = \frac{\mu_o}{4\pi}\oint_{circuit\,A}\oint_{circuit\,B}\frac{d\overline{s_A}\cdot d\overline{s_B}}{r_{AB}} \quad (C.1)$$

where $$r_{AB} = |\overline{s_B} - \overline{s_A}|$$

and $\mu_o = 4\pi 10^{-7}$ henries/meter

Here, we consider the case where both circuits are composed of straight-line segments.

Circuit A is composed of segments $A_1 \ldots A_n$.
Circuit B is composed of segments $B_1 \ldots B_m$.
Then C.1 becomes:

$$L_m = \frac{\mu_o}{4\pi}\sum_{k=1}^{n}\sum_{l=1}^{m}\int_{B_l^{start}}^{B_l^{finish}}\int_{A_k^{start}}^{A_k^{finish}}\frac{d\overline{s_A}\cdot d\overline{s_B}}{r_{AB}} \quad (C.2)$$

The integral over $A_k$ can be evaluated analytically:

$$L_m = \frac{\mu_o}{4\pi}\sum_{k=1}^{n}\sum_{l=1}^{m}\frac{\overline{s_l}\cdot\overline{s_k}}{\sqrt{s_k^2}}$$

$$\int_{b=0}^{b=1}\log\left(\frac{\sqrt{\frac{(\overline{s_k}+s_g\overline{s_b})\cdot(\overline{s_k}+s_g\overline{s_b})}{s_b^2}} + \sqrt{\frac{s_k^2}{s_b^2}}+s_g c_l}{1+s_g c_l}\right)db \quad (C.3)$$

where
$\overline{s_k}^{start}$=vector from origin to start of segment $A_k$
$\overline{s_k}^{finish}$=vector from origin to finish of segment $A_k$
$\overline{s_l}^{start}$=vector from origin to start of segment $B_l$
$\overline{s_l}^{finish}$=vector from origin to finish of segment $B_l$
$\overline{s_k} = \overline{s_k}^{finish} - \overline{s_k}^{start}$
$\overline{s_l} = \overline{s_l}^{finish} - \overline{s_l}^{start}$
$s_k^2 = \overline{s_k}\cdot\overline{s_k}$
$s_l^2 = \overline{s_l}\cdot\overline{s_l}$
$\overline{s_s} = (\overline{s_l}^{start} - \overline{s_k}^{start})$
$s_g = +1$ if $(\overline{s_s}\cdot\overline{s_k} \geq 0)$, $-1$ if $(\overline{s_s}\cdot\overline{s_k} < 0)$
$\overline{s_e} = \overline{s_l}^{finish}$ if $(s_g = +1)$, $\overline{s_k}^{start}$ if $(s_g = -1)$
$\overline{s_b} = \overline{s_l}^{start} - \overline{s_e} + \overline{s_l}b$
$s_b^2 = \overline{s_b}\cdot\overline{s_b}$ $$c_l = \frac{\overline{s_b}\cdot\overline{s_k}}{\sqrt{s_b^2 s_k^2}} = \text{cosine of angle between } \overline{s_b} \text{ and } \overline{s_k}$$

Equation C.3 is easily evaluated numerically by well-known numerical integration methods.

Equation C.3 combines two forms, which integrate in opposite directions along segment $A_k$. The two forms are combined because each form has a region of potential numerical instability due to a zero denominator.

The first region of numerical instability occurs when $\overline{s}_s$ and $\overline{s}_b$ approach being parallel. In this region, $\overline{s}_s \cdot \overline{s}_b > 0$, and $1-c_t$ approaches zero. When $\overline{s}_s$ and $\overline{s}_b$ become exactly parallel, $1-c_t=0$ exactly. In this region, we choose $s_g=+1$ to avoid a zero denominator in the integral in equation C.3.

The second region of numerical instability occurs when $\overline{s}_s$ and $\overline{s}_b$ approach being antiparallel. In this region, $\overline{s}_s \cdot \overline{s}_b < 0$, and $1+c_t$ approaches zero. When $\overline{s}_s$ and $\overline{s}_b$ become exactly parallel, $1+c_t=0$ exactly. In this region, we choose $s_g=-1$ to avoid a zero denominator in the integral in equation C.3.

To derive equation C.3, start with the term in equation C.1 for one pair of current segments:

$$I_{kl} = \int_{B_l^{start}}^{B_l^{finish}} \int_{A_k^{start}}^{A_k^{finish}} \frac{d\overline{s_A} \cdot d\overline{s_B}}{r_{AB}} \quad \text{(C.4)}$$

Current segments $A_k$ and $B_l$ are both straight lines, so it is natural to describe them in linear terms of dimensionless variables a and b respectively, where $0 \leq a \leq 1$
$0 \leq b \leq 1$ We integrate over a symbolically first, so we will keep dependendencies on a explicit. Dependencies on b are absorbed into quantities independent of a while we integrate over a.

A point on segment $A_k$ is one of two linear functions of a, depending on $s_g$:

When $s_g=+1$, then $\overline{s_A(a)} = \overline{s_k^{finish}} - \overline{s_k}a$
When $s_g=-1$, then $\overline{s_A(a)} = \overline{s_k^{start}} + \overline{s_k}a$ A point on segment $B_l$ is a linear function of b:
$\overline{s_B(b)} = \overline{s_l^{start}} + \overline{s_l}b$ Then:
$d\overline{s_A} = -s_g \overline{s_k} da$
$d\overline{s_B} = \overline{s_l} db$
$d\overline{s_A} \cdot d\overline{s_B} = -s_g \overline{s_k} \cdot \overline{s_l} da\, db$
$r_{AB} = \sqrt{(\overline{s_b} + s_g \overline{s_k}a) \cdot (\overline{s_b} + s_g \overline{s_k}a)}$ Now equation C.4 becomes:

$$I_{kl} = -s_g \overline{s_k} \cdot \overline{s_l} \int_0^1 \int_{(1+s_g)/2}^{(1-s_g)/2} \frac{da}{\sqrt{(\overline{s_b} + s_g \overline{s_k}a) \cdot (\overline{s_b} + s_g \overline{s_k}a)}} db \quad \text{(C.5)}$$

Expand the denominator in equation C.5, separate out the coefficient of $a^2$, aid remove the $s_g$ dependence from the limits of integration:

$$I_{kl} = \frac{\overline{s_k} \cdot \overline{s_l}}{\sqrt{s_k^2}} \int_0^1 \int_0^1 \frac{da}{\sqrt{\frac{s_b^2}{s_k^2} + \frac{2s_g \overline{s_b} \cdot \overline{s_b}}{s_k^3}a + a^2}} db \quad \text{(C.6)}$$

Define two quantities which do not depend on a:

$$\alpha = \frac{s_g \overline{s_b} \cdot \overline{s_k}}{s_k^2} = \sqrt{\frac{s_b^2}{s_k^2}} s_g c_l$$

$$\beta = \frac{s_b^2}{s_k^2} - \alpha^2 = \frac{s_b^2}{s_k^2}(1 - c_t^2)$$

Note that $0 \leq \beta \leq 2$.

Define a new variable x:

$x = a + \alpha$

Now equation C.6 becomes:

$$I_{kl} = \frac{\overline{s_k} \cdot \overline{s_l}}{\sqrt{s_k^2}} \int_0^1 \int_\alpha^{\alpha+1} \frac{dx}{\sqrt{x^2 + \beta}} db \quad \text{(C.7)}$$

We have for $\beta \geq 0$:

$$\int \frac{dx}{\sqrt{x^2 + \beta}} = \log(x + \sqrt{x^2 + \beta}) \quad \text{(C.8)}$$

Substitute equation C.8 into equation C.7:

$$I_{kl} = \frac{\overline{s_k} \cdot \overline{s_l}}{\sqrt{s_k^2}} \int_0^1 \log\left(\frac{\alpha + 1 + \sqrt{(\alpha+1)^2 + \beta}}{\alpha + \sqrt{\alpha^2 + \beta}}\right) db \quad \text{(C.9)}$$

Substitute the definitions of $\alpha$ and $\beta$ into equation C.9:

$$I_{kl} = \frac{\overline{s_k} \cdot \overline{s_l}}{\sqrt{s_k^2}} \quad \text{(C.10)}$$

$$\int_0^1 \log\left(\frac{\sqrt{\frac{s_b^2}{s_k^2}} s_g c_t + 1 + \sqrt{\left(\sqrt{\frac{s_b^2}{s_k^2}} s_g c_t + 1\right)^2 + \frac{s_b^2}{s_k^2}(1 - c_t^2)}}{\sqrt{\frac{s_b^2}{s_k^2}} s_g c_t + \sqrt{\left(\sqrt{\frac{s_b^2}{s_k^2}} s_g c_t\right)^2 + \frac{s_b^2}{s_k^2}(1 - c_t^2)}}\right) db$$

Remove a common factor of $$\sqrt{\frac{s_b^2}{s_k^2}}$$

from numerator and denominator:

$$I_{kl} = \frac{\overline{s_k} \cdot \overline{s_l}}{\sqrt{s_k^2}} \int_0^1 \log\left(\frac{s_g c_t + \sqrt{\frac{s_k^2}{s_b^2}} + \sqrt{\left(s_g c_t + \sqrt{\frac{s_b^2}{s_k^2}}\right)^2 + (1 - c_t^2)}}{s_g c_t + \sqrt{(s_g c_t)^2 + (1 - c_t^2)}}\right) db \quad (C.11)$$

Simplify:

$$I_{kl} = \frac{\overline{s_k} \cdot \overline{s_l}}{\sqrt{s_k^2}} \int_0^1 \log\left(\frac{s_g c_t + \sqrt{\frac{s_k^2}{s_b^2}} + \sqrt{\frac{2 s_g c_t \sqrt{s_k^2 s_b^2} + s_k^2 + s_b^2}{s_b^2}}}{s_g c_t + 1}\right) db \quad (C.12)$$

Substitute for $c_t$ in the last radical in the numerator:

$$I_{kl} = \frac{\overline{s_k} \cdot \overline{s_l}}{\sqrt{s_k^2}} \int_0^1 \log\left(\frac{s_g c_t + \sqrt{\frac{s_k^2}{s_b^2}} + \sqrt{\frac{2 s_g \overline{s_b} \cdot \overline{s_k} + s_k^2 + s_b^2}{s_b^2}}}{s_g c_t + 1}\right) db \quad (C.13)$$

Factor the numerator inside the last radical in the numerator:

$$I_{kl} = \frac{\overline{s_k} \cdot \overline{s_l}}{\sqrt{s_k^2}} \int_0^1 \log\left(\frac{s_g c_t + \sqrt{\frac{s_k^2}{s_b^2}} + \sqrt{\frac{(\overline{s_k} + s_g \overline{s_b}) \cdot (\overline{s_k} + s_g \overline{s_b})}{s_b^2}}}{s_g c_t + 1}\right) db \quad (C.14)$$

Substitute equation C.14 into equation C.4, and that into equation C.2:

$$L_m = \frac{\mu_o}{4\pi} \sum_{k=1}^{n} \sum_{l=1}^{m} \frac{\overline{s_k} \cdot \overline{s_l}}{\sqrt{s_k^2}}$$

$$\int_0^1 \log\left(\frac{s_g c_t + \sqrt{\frac{s_k^2}{s_b^2}} + \sqrt{\frac{(\overline{s_k} + s_g \overline{s_b}) \cdot (\overline{s_k} + s_g \overline{s_b})}{s_b^2}}}{s_g c_t + 1}\right) db \quad (C.15)$$

This is our result, equation C.3.

The invention claimed is:

1. An electromagnetic tracking system comprising:
a magnetic field generating unit having at least one field generating coil driven by a drive signal,
a field sensing unit having at least one field sensing coil generating a sensing signal responsive to a changing magnetic field, said changing magnetic field including a position-dependent field produced by said magnetic field generating unit,
the generating and sensing units being arranged to generate and to sense, respectively, an electromagnetic field in an arena of interest, and wherein at least one of said units is movable,
signal measurement and conditioning circuitry connected to said units to (i) synchronously sample and digitize drive signal data and sensing signal data for respective pairs of field generating and field sensing coils, cumulating the digitized data to form a raw signal matrix, and (ii) determine a mutual inductance matrix from the raw signal matrix, and
a processor that utilizes the mutual inductance matrix to determine coordinates of the movable unit.

2. The electromagnetic tracking system of claim 1, wherein the field sensing unit is fixed to a structure and the field generating unit is movable.

3. The electromagnetic tracking system of claim 2, wherein the processor determines coordinates of the movable unit by approximating coordinates of the field sensing unit relative to the field generating unit, and iteratively adjusting the approximated coordinates to determine coordinates of the movable unit.

4. The electromagnetic tracking system of claim 1, wherein the processor normalizes the raw signal matrix with respect to drive signal and sensing unit coil coupling response.

5. The electromagnetic tracking system of claim 1, wherein the drive signal is any of a drive current or a drive voltage.

6. An electromagnetic tracking system comprising
a magnetic field generating unit and a magnetic field sensing unit, at least one said units being movable relative to the other, the sensing unit having a sensing signal responsive to a changing magnetic field produced by said magnetic field generating unit
the generating and sensing units being arranged to generate and to sense, respectively an electromagnetic field in an arena of interest,
signal measurement and conditioning circuitry connected to said units to sample and condition field generating and field sensing signal values,
a processor operative on sampled and conditioned signal values to determine relative position and orientation of said units,
wherein the signal measurement and conditioning circuitry includes a common gain stage amplifier connected to plural coils and a high precision analog to digital converter that converts amplified coil signals to high precision digital values such that coil outputs over a work arena may be digitally processed without patching or conversion of gains in different regions of the work arena.

7. An electromagnetic tracking system comprising
a magnetic field generating unit driven by a drive signal,
a field sensing unit having a sensing signal responsive to a changing magnetic field, said changing magnetic field including a position-dependent field produced by said magnetic field generating unit,
the generating and sensing units being arranged to generate and to sense, respectively, an electromagnetic field in an arena of interest, and wherein at least one of said units is movable,
signal measurement and conditioning circuitry connected to said units to sample and digitize signal data for the field generating and field sensing units,
a distorter having a structure optimal for shielding one or more objects in the arena of interest, said distorter being disposed so as to substantially shield magnetic fields generated by said objects, and a processor operative on the sampled and digitized signal data to determine relative coordinates and orientations of said field generating or field sensing unit, said processor modeling the distorter and the generating and sensing units to generate modeled signal data and fitting said modeled signal data to measured signal values to determine coordinates and orientations of said field generating and field sensing units.

* * * * *